United States Patent
Strugnell et al.

(10) Patent No.: US 7,094,775 B2
(45) Date of Patent: Aug. 22, 2006

(54) METHOD OF TREATING BREAST CANCER USING A COMBINATION OF VITAMIN D ANALOGUES AND OTHER AGENTS

(75) Inventors: Stephen A. Strugnell, Madison, WI (US); Don Wigington, Middleton, WI (US)

(73) Assignee: Bone Care International, LLC, Middleton, WI (US)

( * ) Notice: Subject to any disclaimer, the term of this patent is extended or adjusted under 35 U.S.C. 154(b) by 194 days.

(21) Appl. No.: 10/881,204

(22) Filed: Jun. 30, 2004

(65) Prior Publication Data

US 2006/0003021 A1    Jan. 5, 2006

(51) Int. Cl.
*A61K 31/56* (2006.01)
*C07C 401/00* (2006.01)

(52) U.S. Cl. ............ 514/167; 514/729; 552/653; 552/657

(58) Field of Classification Search .......... 514/729, 514/167; 552/653, 657
See application file for complete search history.

(56) References Cited

U.S. PATENT DOCUMENTS

| | | |
|---|---|---|
| 2,383,446 A | 8/1945 | Calcott et al. |
| 3,697,559 A | 10/1972 | DeLuca et al. |
| 3,741,996 A | 6/1973 | DeLuca et al. |
| 3,907,843 A | 9/1975 | DeLuca et al. |
| 4,022,891 A | 5/1977 | Takeshita et al. |
| 4,159,326 A | 6/1979 | Barton et al. |
| 4,160,803 A | 7/1979 | Potts |
| 4,195,027 A | 3/1980 | DeLuca et al. |
| 4,202,829 A | 5/1980 | DeLuca et al. |
| 4,225,596 A | 9/1980 | DeLuca et al. |
| 4,234,495 A | 11/1980 | DeLuca et al. |
| 4,260,549 A | 4/1981 | DeLuca et al. |
| 4,310,511 A | 1/1982 | Holick |
| 4,338,250 A | 7/1982 | DeLuca et al. |
| 4,341,774 A | 7/1982 | Aoki et al. |
| 4,362,710 A | 12/1982 | Watanabe |
| 4,364,941 A | 12/1982 | Kiyoki et al. |
| 4,388,243 A | 6/1983 | Nishikawa et al. |
| 4,391,802 A | 7/1983 | Suda et al. |
| 4,448,721 A | 5/1984 | DeLuca et al. |
| 4,481,198 A | 11/1984 | DeLuca et al. |
| 4,508,651 A | 4/1985 | Baggiolini et al. |
| 4,554,106 A | 11/1985 | DeLuca et al. |
| 4,555,364 A | 11/1985 | DeLuca et al. |
| 4,588,716 A | 5/1986 | DeLuca et al. |

(Continued)

FOREIGN PATENT DOCUMENTS

EP    0197514    10/1986

(Continued)

OTHER PUBLICATIONS

Beer, et al., "Weekly High-Dose Calcitriol and Docetaxel in Metastatic Androgen-Independent Prostate Cancer," *J. Clinical Oncology*, (2003) 21:1:123-128.

(Continued)

*Primary Examiner*—Sabiha N Qazi
(74) *Attorney, Agent, or Firm*—Teresa J. Welch; Jeffrey D. Peterson; Michael Best & Friedrich LLP

(57) ABSTRACT

The invention provides therapeutic methods for inhibiting, ameliorating or alleviating the hyperproliferative cellular activity of diseases of the breast, e.g., breast cancer, which includes administering to a patient in need thereof an active vitamin D analogue and another anticancer agent. Cell differentiation is promoted, induced or enhanced without causing to the patient dose-limiting hypercalcemia and hypercalciuria.

11 Claims, 21 Drawing Sheets

U.S. PATENT DOCUMENTS

| | | | |
|---|---|---|---|
| 4,652,405 A | 3/1987 | Partridge et al. | |
| 4,661,294 A | 4/1987 | Holick et al. | |
| 4,670,190 A | 6/1987 | Hesse et al. | |
| 4,689,180 A | 8/1987 | DeLuca et al. | |
| 4,698,328 A | 10/1987 | Neer et al. | |
| 4,717,721 A | 1/1988 | DeLuca et al. | |
| 4,728,643 A | 3/1988 | Holick et al. | |
| 4,749,710 A | 6/1988 | Truitt et al. | |
| 4,758,383 A | 7/1988 | Tachibana | |
| 4,804,502 A | 2/1989 | Baggiolini et al. | |
| 4,833,125 A | 5/1989 | Neer et al. | |
| 4,866,048 A | 9/1989 | Calverley et al. | |
| RE33,107 E | 11/1989 | Dikstein et al. | |
| 4,891,364 A | 1/1990 | Kubodera et al. | |
| 4,897,388 A | 1/1990 | Mallucke | |
| 4,902,481 A | 2/1990 | Clark et al. | |
| 4,948,789 A | 8/1990 | Slatopolsky | |
| 5,030,772 A | 7/1991 | DeLuca et al. | |
| 5,035,783 A | 7/1991 | Goethals et al. | |
| 5,037,816 A | 8/1991 | Holick et al. | |
| 5,063,221 A | 11/1991 | Nishii et al. | |
| 5,087,619 A | 2/1992 | Baggiolini et al. | |
| 5,098,899 A | 3/1992 | Gilbert et al. | |
| 5,104,864 A | 4/1992 | DeLuca et al. | |
| 5,141,719 A | 8/1992 | Fernwood et al. | |
| 5,145,846 A | 9/1992 | Baggiiolini et al. | |
| 5,157,135 A | 10/1992 | Tsuji et al. | |
| 5,190,935 A | 3/1993 | Binderup et al. | |
| 5,194,248 A | 3/1993 | Holick | |
| 5,205,989 A | 4/1993 | Aysta | |
| 5,206,229 A | 4/1993 | Calverley et al. | |
| 5,219,528 A | 6/1993 | Clark | |
| 5,232,836 A | 8/1993 | Bouillon et al. | |
| 5,250,523 A | 10/1993 | DeLuca et al. | |
| 5,252,191 A | 10/1993 | Pauli et al. | |
| 5,260,290 A | 11/1993 | DeLuca et al. | |
| 5,264,184 A | 11/1993 | Aysta et al. | |
| 5,264,618 A | 11/1993 | Felgner et al. | |
| 5,304,291 A | 4/1994 | Bout et al. | |
| 5,321,018 A | 6/1994 | DeLuca | |
| 5,334,740 A | 8/1994 | Takahashi et al. | |
| 5,338,532 A | 8/1994 | Tomalia et al. | |
| 5,366,965 A | 11/1994 | Strein | |
| 5,372,996 A | 12/1994 | Labrie | |
| 5,374,629 A | 12/1994 | Calverley et al. | |
| 5,403,831 A * | 4/1995 | DeLuca et al. | 514/167 |
| 5,417,923 A | 5/1995 | Bojanic et al. | |
| 5,448,120 A | 9/1995 | Schaule et al. | |
| 5,449,668 A | 9/1995 | Sestelo et al. | |
| 5,486,636 A | 1/1996 | DeLuca et al. | |
| 5,488,120 A | 1/1996 | Knutson et al. | |
| 5,499,668 A | 3/1996 | Katayama et al. | |
| 5,512,554 A | 4/1996 | Baggiolini et al. | |
| 5,518,725 A | 5/1996 | Daynes et al. | |
| 5,527,524 A | 6/1996 | Tomalia et al. | |
| 5,529,991 A | 6/1996 | Knutson et al. | |
| 5,540,919 A | 7/1996 | Daynes et al. | |
| 5,554,386 A | 9/1996 | Groman et al. | |
| 5,559,104 A | 9/1996 | Romeo et al. | |
| 5,559,107 A | 9/1996 | Gates et al. | |
| 5,561,123 A | 10/1996 | DeLuca et al. | |
| 5,562,910 A | 10/1996 | Daynes et al. | |
| 5,585,368 A | 12/1996 | Steinmeyer et al. | |
| 5,589,471 A | 12/1996 | Hansen et al. | |
| 5,597,575 A | 1/1997 | Breitbarth | |
| 5,602,116 A * | 2/1997 | Knutson et al. | 514/167 |
| 5,612,327 A | 3/1997 | Makino et al. | |
| 5,614,513 A | 3/1997 | Knutson et al. | |
| 5,637,742 A | 6/1997 | Valles et al. | |
| 5,661,025 A | 8/1997 | Szoka, Jr. et al. | |
| 5,663,157 A | 9/1997 | Steinmeyer et al. | |
| 5,665,387 A | 9/1997 | Mathieu et al. | |
| 5,665,716 A | 9/1997 | Kirsch et al. | |
| 5,691,328 A | 11/1997 | Peterson et al. | |
| 5,700,791 A | 12/1997 | Steinmeyer et al. | |
| 5,707,980 A | 1/1998 | Knutson et al. | |
| 5,710,142 A | 1/1998 | Calverley et al. | |
| 5,710,294 A | 1/1998 | DeLuca et al. | |
| 5,716,946 A | 2/1998 | DeLuca et al. | |
| 5,739,271 A | 4/1998 | Sridhar et al. | |
| 5,750,517 A | 5/1998 | Baggiolini et al. | |
| 5,750,746 A | 5/1998 | DeLuca et al. | |
| 5,753,638 A | 5/1998 | Baggiolini et al. | |
| 5,763,428 A | 6/1998 | Knutson et al. | |
| 5,763,429 A | 6/1998 | Bishop et al. | |
| 5,786,348 A * | 7/1998 | Bishop et al. | 514/167 |
| 5,789,397 A * | 8/1998 | Bishop et al. | 514/167 |
| 5,789,399 A | 8/1998 | Strube | |
| 5,795,882 A | 8/1998 | Bishop et al. | |
| 5,798,345 A * | 8/1998 | Knutson et al. | 514/167 |
| 5,801,164 A | 9/1998 | Knutson et al. | |
| 5,834,016 A | 11/1998 | Naeff et al. | |
| 5,869,473 A | 2/1999 | Knutson et al. | |
| 5,880,114 A | 3/1999 | DeLuca et al. | |
| 5,902,806 A | 5/1999 | Ikeda et al. | |
| 5,905,074 A | 5/1999 | Schneider | |
| 5,952,317 A | 9/1999 | DeLuca et al. | |
| 5,962,731 A | 10/1999 | Boehm et al. | |
| 5,972,917 A * | 10/1999 | Bishop et al. | 514/167 |
| 5,976,784 A | 11/1999 | DeLuca et al. | |
| 6,025,346 A | 2/2000 | Knutson et al. | |
| 6,087,350 A | 7/2000 | Johnson et al. | |
| 6,103,709 A | 8/2000 | Norman et al. | |
| RE36,854 E | 9/2000 | Sestelo | |
| 6,143,910 A * | 11/2000 | Bishop et al. | 552/653 |
| 6,147,064 A | 11/2000 | Knutson et al. | |
| 6,150,346 A | 11/2000 | Knutson et al. | |
| 6,166,000 A * | 12/2000 | Bishop et al. | 514/167 |
| 6,211,168 B1 * | 4/2001 | Bishop et al. | 514/167 |
| 6,218,430 B1 | 4/2001 | Allegretto et al. | |
| 6,221,911 B1 | 4/2001 | Lavin et al. | |
| 6,242,434 B1 * | 6/2001 | Bishop et al. | 514/167 |
| 6,242,435 B1 | 6/2001 | Achkar | |
| 6,251,883 B1 * | 6/2001 | Horst et al. | 514/167 |
| 6,329,357 B1 | 12/2001 | Norman et al. | |
| 6,369,098 B1 | 4/2002 | Pershadsingh et al. | |
| 6,369,099 B1 | 4/2002 | DeLuca et al. | |
| 6,395,784 B1 | 5/2002 | Ryono | |
| 6,432,962 B1 | 8/2002 | Horneman | |
| 6,458,827 B1 | 10/2002 | DeLuca et al. | |
| 6,482,812 B1 | 11/2002 | DeLuca et al. | |
| 6,506,912 B1 | 1/2003 | DeLuca et al. | |
| 6,521,222 B1 | 2/2003 | Philippe et al. | |
| 6,521,608 B1 | 2/2003 | Henner et al. | |
| 6,524,594 B1 | 2/2003 | Santora et al. | |
| 6,531,460 B1 | 3/2003 | Takenouchi et al. | |
| 6,537,982 B1 * | 3/2003 | Bishop et al. | 514/168 |
| 6,538,037 B1 * | 3/2003 | Bishop et al. | 514/729 |
| 6,541,670 B1 | 4/2003 | Ottosen | |
| 6,548,489 B1 | 4/2003 | Takenouchi et al. | |
| 6,552,009 B1 | 4/2003 | Achkar | |
| 6,555,710 B1 | 4/2003 | Ottosen | |
| 6,559,139 B1 | 5/2003 | Johnson et al. | |
| 6,566,554 B1 | 5/2003 | Ottosen | |
| 6,582,710 B1 | 6/2003 | Deckers et al. | |
| 6,599,513 B1 | 7/2003 | Deckers et al. | |
| 6,642,218 B1 | 11/2003 | Steinmeyer et al. | |
| 6,680,309 B1 * | 1/2004 | Bishop et al. | 514/167 |
| 2001/0002396 A1 | 5/2001 | Achkar | |
| 2001/0025036 A1 | 9/2001 | DeLuca et al. | |
| 2001/0049365 A1 | 12/2001 | Achkar | |
| 2001/0051617 A1 | 12/2001 | DeLuca et al. | |
| 2002/0006917 A1 | 1/2002 | DeLuca et al. | |
| 2002/0049344 A1 | 4/2002 | Steinmeyer et al. | |

| | | | |
|---|---|---|---|
| 2002/0068723 | A1 | 6/2002 | DeLuca et al. |
| 2002/0091109 | A1 | 7/2002 | Takenouchi et al. |
| 2002/0099039 | A1 | 7/2002 | Takenouchi et al. |
| 2002/0103173 | A1 | 8/2002 | Takenouchi et al. |
| 2002/0132799 | A1 | 9/2002 | Takenouchi et al. |
| 2003/0040508 | A1 | 2/2003 | DeLuca et al. |
| 2003/0109506 | A1 | 6/2003 | Hayes et al. |
| 2003/0119795 | A1 | 6/2003 | Henner et al. |
| 2003/0149005 | A1 | 8/2003 | Posner et al. |
| 2003/0149006 | A1 | 8/2003 | Steinmeyer et al. |
| 2003/0166622 | A1 | 9/2003 | Steinmeyer et al. |
| 2003/0171342 | A1 | 9/2003 | Posner et al. |
| 2003/0195171 | A1 | 10/2003 | Daifotis et al. |
| 2003/0195176 | A1 | 10/2003 | Kawase et al. |
| 2003/0195259 | A1 | 10/2003 | Bernardon et al. |
| 2003/0216359 | A1 | 11/2003 | Johnson et al. |
| 2004/0019023 | A1 | 1/2004 | Morikawa et al. |

FOREIGN PATENT DOCUMENTS

| | | |
|---|---|---|
| EP | 62000033 | 10/1986 |
| EP | 0390097 | 10/1990 |
| EP | 0503630 | 9/1992 |
| EP | 0562497 | 9/1993 |
| EP | 5320127 | 9/1993 |
| EP | 6025039 | 2/1994 |
| EP | 0664287 | 7/1995 |
| WO | WO 84/04527 | 11/1984 |
| WO | WO 87/00834 | 2/1987 |
| WO | WO 90/01321 | 2/1990 |
| WO | WO 90/10620 | 9/1990 |
| WO | WO 92/05130 | 4/1992 |
| WO | WO 92/12165 | 7/1992 |
| WO | WO 92/21355 | 12/1992 |
| WO | WO 93/07883 | 4/1993 |
| WO | WO 93/14763 | 8/1993 |
| WO | WO 94/00128 | 1/1994 |
| WO | WO 94/05630 | 3/1994 |
| WO | WO 94/16711 | 8/1994 |
| WO | WO 96/31215 | 10/1996 |
| WO | WO 96/40153 | 12/1996 |
| WO | WO 96/40154 | 12/1996 |
| WO | WO 97/00242 | 1/1997 |
| WO | WO 97/20811 | 6/1997 |
| WO | WO 97/23242 | 7/1997 |
| WO | WO 98/56387 | 12/1998 |
| WO | WO 98/56389 | 12/1998 |
| WO | WO 99/16451 | 4/1999 |
| WO | WO 99/49027 | 9/1999 |
| WO | WO 99/49870 | 10/1999 |
| WO | WO 00/03700 | 1/2000 |
| WO | WO 01/22974 | 4/2001 |
| WO | WO 01/64251 | 9/2001 |

OTHER PUBLICATIONS

Johnson et al., "Vitamin D-related Therapies in Prostate Cancer," *Cancer & Metastasis Reviews* (2002) 21:147-158.

Muindi et al., "Pharmacokinetics of High-Dose Oral Calcitriol: Results from a Phase 1 Trial of Calcitriol and Paclitaxel," *Clinical Pharm. & Therap.* 72:6:648-659 (2002).

Norman et al., "Vitamin D Endocrine System-Structural, Biological, Genetic and Clinical Aspects," Proceedings of Eleventh Workshop on Vitamin D, Nashville, TN May 27-Jun. 1, 2000.

Swami, et al., "1α,25-Dihydroxyvitamin $D_3$ Down-Regulates Estrogen Receptor Abundance and Suppresses Estrogen Actions in MCF-7 Human Breast Cancer Cells," *Clinic. Cancer Res.* (2000) 6:3371-3379.

Wigington, et al., "1,24$(OH)_2D_2$ is as Effective as 1,25$(OH)_2D_3$ or 1,25$(OH)_2D_2$ at Inhibiting Cancer Cell Proliferation in Combination Studies with Chemotherapeutic Drugs," Abstract (2003).

"Oregon Health & Science University and Novacea Announce Broad Patent for Unique Formulation and Use of Vitamin D for Cancer Treatment," *Life Extension Foundation, Daily News* (Mar. 18, 2003).

Aloia, J. et al., "Calcitriol in the Treatment of Postmenopausal Osteoporosis," *Amer. J. Med.*, (1988) 84:401-08.

Barton, D. et al., "Synthetic Uses of Steroidal Ring & Diene Protection: 22,23-Dihydroergosterol," *JCS Perkin I*, (1976) pp. 821-826.

Beer, T. et al., "Weekly High-Dose Calcitriol and Docetaxel in Metastatic Androgen-Independent Prostate Cancer," *Journal of Clinical Oncology*, (Jan. 2003) 21:1:123-128.

Beer, et al., "A Phase I Trial of Pulse Calcitriol in Patients with Refractory Malignancies," *Cancer*, (Jun. 15, 2001) 91:12:2431-2439.

Beer, et al., "Weekly High-Dose Calcitriol and Docetaxel in Advanced Prostate Cancer," *Seminars in Oncology*, Suppl 15 (Aug. 2001) 28:4:49-55.

Blazsek, I. et al. "Combined Differentiation Therapy in Myelodysplastic Syndrome with Retinoid Acid 1α,25 Dihydroxyvitamin $D_3$, and Prednisone," 16:4:259-264 (Abstract).

Braunwald, E. et al., *Harrison's Principles of Internal Medicine*: Part Eleven, "Disorders of Bone and Mineral Metabolism," Chapter 335, McGraw-Hill, New York, (1987) pp. 1860-1865.

Brautbar, N. "Osteoporosis: Is 1,25-(OH)2D3 of Value in Treatment?" *Nephron* (1986) 44:161-166.

Brown, J.P. et al., "Serum Bone Gala-Protein: A Specific Marker for Bone Formation in Postmenopausal Osteoporosis," *Lancet*, (1984) 1:1091-1093.

Buras, R. et al., "Vitamin D Receptors in Breast Cancer Cells," *Breast Cancer Res. & Treatment*, (1994) 31:191-202.

Calverley, M., "Synthesis of MC 903, A Biologically Active Vitamin D Metabolite Analogue," *Triahedron* (1987) 43:20:4609-4619.

Caniggia, A. et al., "Effect of a Long-Term Treatment with 1,25-Dihydroxyvitamin $D_3$ on Osteocalcin in Postmenopausal Osteoporosis," *Cacified Tissue Int.*, (1986) 38:328-332.

Cho, Y.L. et al., "Combined Effects of 1,25-Dihydroxyvitamin $D_3$ and Platinum Drugs on the Growth of MCF-7 Cells," *Cancer Research*, (Jun. 1991) 51:2848-2853.

Christiansen, C. et al., "Effect of 1,25-Dihydroxy-Vitamin $D_3$ is Itself or Combined with Hormone Treatment in Preventing Postmenopausal Osteoporosis," *Eur. J. Clin. Invest.*, (1981) 11:305-309.

Christiansen, C. et al., "Prevention of Early Postmenopausal Bone Loss: Controlled 2-Year Study in 315 Normal Females," *Europ J Clin Inves.*, (1980) 10:273-279.

Crump, D.R. et al., "(22S-Hydroxyvitamin $D_4$," *J.C.S. Perkins Trans, I*, (1973) pp. 2731-2733.

Defacque, H. et al., "Different Combinations of Retinoids and Vitamin $D_3$ Analogs Efficiently Promote Growth Inhibition and Differentiation of Myelomonocytic Leukemia Cell Lines," *J. Pharmacology and Experimental Therapeutics*, (1994) 271:193-199.

DeLuca et al., "Synthesis, Biological Activity, and Metabolism of 22,23-$^3$H-Vitamin $D_4$," *Arch. Biochem. Biophys.*, (1968) 124:122-128.

Duda et al., "1,25-Dihydroxyvitamin D Stimulation Test for Osteoblast Function in Normal and Osteoporotic Postmenopausal Women," *J. Clinic Inves.*, (1987) 79:1249-1253.

Endo, K. et al., "Effect of Combination Treatment with Vitamin D Analog (OCT) and a Bisphosphonate (AHPrBP) in a Nude Mouse Model of Cancer-Associated Hyperclacemia," *Journal of Bone and Mineral Research*, (1998) 13:9:1378-1383.

Engstrom, G. et al. "Metabolism of Vitamin D2 in Pig Liver Homogenates: Evidence for a Free Radical Reaction" *Archives of Biochemistry and Biophysics* (1989) 270:2:432-440.

Foldes, J. et al., "Long Term Treatment with 1α(OH)$D_3$ for Postmenopausal Osteoporosis: Efficacy and Safety," *Osteoporosis*, (1987) 2:971-973.

Gallagher, J.C., et al., "Treatment of Postmenopausal Osteoporosis with High Doses of Synthetic Calcitriol," *Annals of Int. Med.*, (1990) 13:649-655.

Gallagher, J.C. et al., "Effects of Increasing Doses of 1α-Hydroxyvitamin D₂ on Calcium Homeostasis in Postmenopausal Osteopenic Women," *J. Bone Min. Res.*, (1994) 9:5:607-614.

Grab, W. Z. "Die Auswertung der Antirachitischen Wirksamkeit Neuer Sterinderivate im Versuch an Ratten und Kuken," *Physiol. Chem.*, (1936) 243:63-89.

Guidelines for the Clinical Evaluation of Drugs Used in the Treatment of Osteoporosis, HEW (FDA) 80-3094, (1979) pp. 5-6.

Hershberger, P. et al. "Calcitriol (1,25-Dihydroxycholecalciferol) Enhances Paclitaxel Antitumor Activity *in Vitro* and *in Vivo* and Accelerates Paclitaxel-induced Apoptosis," *Clinical Cancer Research*, (Apr. 2001) 7:1043-1051.

Hoikka, V. et al., "Treatment of Osteoporosis with 1-Alpha-Hydroxycholecalciferol and Calcium," *Acta. Med. Scand.*(1980) 207:221-224.

Holick, M.F., "Noncalcemic Actions of 1,25-Dihydroxyvitamin D₃ and Clinical Applications", *Bone*, (1995) 17:2:107S-110S.

Holick, M.F. et al., "1α-Hydroxy Derivative of Vitamin D₃: A Highly Potent Analog of 1α,25 Dihydroxyvitamin D₃," *Science* (1973) pp. 180, 190-191.

Holick, M.F. et al., "Identification of 1,25-Dihydroxycholecalciferol, a Form of Vitamin D₃ Metobolically Active in the Intestine," *Proc. Natl. Acad. Sci. USA*, (1971) 68:803-804.

Horst et al., "Discrimination in the Metabolism of Orally Dosed Ergocalciferol and Cholecalciferol by the Pig, Rat and Chick," *Biochem. J.*, (1982) 204:185-189.

Horst et al., "Quantitation of Vitamin D and its Metabolites and Their Plasma Concentrations in Five Species of Animals," *Anal. Biochem.*, (1981) 116:189-203.

Horst et al., "1-α-Hydroxylation of 24-Hydroxyvitamin D₂ Represents a Minor Physiological Pathway for the Activation of Vitamin D₂ in Mammals," *Biochemistry* (1990) 29:578-582.

Jensen, G.F. et al., "Treatment of Post Menopausal Osteoporosis. A Controlled Therapeutic Trial Comparing Oestrogen/Gestagen, 1,25-Dihydroxy-Vitamin D₃ and Calcium," *Clin. Endocrinol.*, (1982) 16:515-524.

Johnson, C. et al., "Vitamin D-related Therapies in Prostate Cancer," *Cancer and Metastasis Review 21*, (2002) pp. 147-158.

Jones, G. et al., "Isolation and Identification of 1,25-Dihydroxyvitamin D₂," *Biochemistry*, (1975) 14:1250-1256.

Kanis, J.A. et al., "Guidelines for Clinical Trials in Osteoporosis, A Position Paper of the European Foundation for Osteoporosis," *Osteoporosis Int.*, (1991) 1:182-188.

Kim, S. et al., Potentiation of 1,25-Dihydroxyvitamin D₃-Induced Differentiation of Human Promyelocytic Leukemia Cells into Monocytes by Costunolide, a Germacranolide Sesquiterpene Lactone, *Biochem. Pharmacology*, (2002) 64:1233-1242.

Knutson, et al., "Metabolism of 1 α-Hydroxyvitamin D₂ to activated Dihydroxyvitamin D₂ Metabolites Decreases Endogenous 1α,25-Dihydroxyvitamin D₃ in Rats and Monkeys," *Endocrinology*, (1995) 136:11:4749-4753.

Kocienski, P.J. et al., "Calciferol and its Relatives. A Synthesis of Vitamin D₄," *J.C.S. Perkins I*, (1979) pp. 1290-1293.

Lam, H.Y. et al., "1α-Hydroxyvitamin D₂: A Potent Synthetic Analog of Vitamin D₂," *Science*, (1974) 486:1038-1040.

Londowski, J.M. et al., "Biological Activity of the C-1, C-3, C-25, β-D-Glucopyranosides of 1,25-Dihydroxyvitamin D₃¹," *J. Pharmacology Expr. Ther.*, (1986) 237:3:837-840.

Majewski, et al., "Inhibition of Tumor Cell-Induced Angiogenisis by Retinoids, 1,25-Dihydroxyvitamin D₃ and their Combination," *Cancer Letters*, (1993) 75:35-39.

Manchand, P. et al., "Nickel-Mediated Conjugate Addition. Elaboration of Calcitriol from Ergocalciferol," *J. Org. Chem.* (1995) 60:6574-6581.

Martin and DeLuca, "Calcium Transport," *Am. J. Physiol.*, 216:1352-1359.

Mathias, C.J. et al., "Tumor-Selective Radiopharmaceutical Targeting Via Receptor-Mediated Endocytosis of Gallium-67-Deferoxamine-Folate," *J. Nucl. Med.* (1996), 37(6):1003-1008.

McDonald, F.G., "The Multiple Nature of Vitamin D," *J. Biol. Chem.* 114, (1936) lxv.

*Merck Index*, S. Budavari (ed.), 11th ed., Merck & Co., Rahway, N.J. (1989) pp. 1579, #9930.

Miller, G. et al., "Vitamin D Receptor Expression, 24-Hydroxylase Activity, and Inhibition of Growth by 1α25,-Dihydroxyvitamin D₃ in Seven Prostatic Carcinoma Cell Lines," *Clin. Cancer Res.* (1995) 1:977-1003.

Miller et al., "The Human Prostatic Carcinoma Cell Line LNCaP Expresses Biologically Active, Specific Receptors for 1α,25-Dihydroxyvitamin D₃¹," *Cancer Res.*, (1992) 52:515-520.

Moffatt, K. et al., "1α,25-Dihydroxyvitamin D₃ and Platinum Drugs Act Synergistically to Inhibit the Growth of Prostate Cancer Cell Lines," *Clinical Cancer Research*, (Mar. 1999) 5:695-703.

Muindi, J. et al., "Pharmacokinetics of High-Dose Oral Calcitriol: Results From a Phase 1 Trial of Calcitriol and Paclitaxel," *Clinical Pharamcology & Therapeutics*, (Dec. 2002) pp. 648-659.

Nemeto, H. et al., "A Stereoselective Synthesis of 1 α—Hydroxy-Vitamin D₃," *CHEMISTRY LETTERS*, (1985) 8:1131-1132.

Nishigaichi, Y. et al., "1,4-Asymmetric Induction from Chiral δ-Oxygenated Allylic Tin Reagents," *Chemistry Letters* (1996) 961-962.

Orimo, H. et al., "Reduced Occurrence of Vertebral Crush Fractures in Senile Osteoporosis Treated with 1α(OH)-Vitamin D₃," *Bone and Mineral*, (1987) 3:47-52.

Ott, S.M. et al., "Calcitriol Treatment is not Effective in Postmenopausal Osteoporosis," *Annals of Int. Med.*, (1989) 1 10:4:267-274.

Paaren et al., "Direct C(1) Hydroxylation of Vitamin D₃ and Related Compounds," *J. Org. Chem.*, (1980) 45:3253-3258.

Packman, K. et al. "Combination Treatment of MCF-7 Xenografts with the Vitamin D₃ Analog EB1089 and Antiestrogens," (Vitamin D Endocrine Workshop, Nashville, TN May 27-Jun. 1, 2000) pp. 511-514.

*Physician's Desk Reference*, Edition 43:1746-1748.

Podenphant, J. et al., "Serum Bone Gla Protein and Other Biochemical Estimates of Bone Turnover in Early Postmenopausal Women During Prophylactic Treatment for Osteoporosis," *Acta Med Scand*, (1985) 218:329-333.

Pouilles, J.M. et al., "Prevention of Early Postmenopausal Bone Loss with 1α-Hydroxy Vitamin D₃, A Three-Year Prospective Study," *Clin Rheumatol.* 11, 4 (1992) pp. 492-497.

Ravid, A. et al., "1,25-Dihydroxyvitamin D₃ Enhances the Susceptibility of Brease Cancer Cells to Doxorubicin-induced Oxidative Damage," *Cancer Research*, (Feb. 15, 1999) 59:862-867.

Reeve, L.E. et al., "Biological Activity of 1α-hydroxy Vitamin D₂ in the Rat," *Arch. Biochem. Biophys.* (Feb. 1978) 186:1:164-167.

Sato, F. et al., "Biological Activity 1α,25-Dihydroxyvitamin D Derivatives—24-epi-1α,25-Dihydroxyvitamin D-2 and 1α,25-Dihydroxyvitamin D-7," Biochim. *Biophys. Acta*, (1991) 1091:188-192.

Shiraki, M. et al., Long-Term Treatment of Postmenopausal Osteoporosis with Active Vitamin D₃1-Alpha-Hydroxycholecalciferol (1α-OHD₃) and 1,24 Dihydroxycholecalciferol (1,24(OH)₂D₃), *Endocrinol. Japan*, (1985) 32:305-315.

Siwinska, A. et al., "Potentiation of the Antiproliferative Effect *in Vitro* of Doxorubicin, Cisplatin and Genistein by New Analogues of Vitamin D," *Anticancer Res.* (2001) 21:1925-1930.

Sjoden, G. et al., "Antirachitic Activity of 1α-Hydroxyergocalciferol and 1α-Hydroxycholecalciferol in Rats," *J. Nutr.*, (1984) 114:2043-2046.

Sjoden, G. et al., "1α-Hydroxyvitamin D₂ is Less Toxic than 1α-Hydroxyvitamin D₃ in the Rat," *Proc. Soc. Exp. Biol. Med.*, (1985) 178:432-436.

Sjoden et al., "Effects of 1,OHD₂ on Bone Tissue," *Acta. Endocrinol.* (Copenh.) (Aug. 1984) 16:4:564-568.

Skowronski et al., "Actions Of Vitamin D₃ Analogs on Human Prostate Cancer Cell Lines: Comparison with 1,25-Dihydroxyvitamin D₃," *Endocrinology*, (1995) 136:20-26.

Skowronski et al., "Vitamin D and Prostate Cancer: 1,25-Dihydroxyvitamin D₃ Receptors and Actions in Human Prostate Cancer Cell Lines," *Endocrinology*, (1993) 132:1952-1960.

Slapak, C. et al., "Treatment of Acute Myeloid Leukemia in the Elderly with Low-Dose Cytarabine, Hydroxyurea, and Calcitriol," *Amer. J. Of Hematology* (1992) 41:178-183.

Smith, A. et al., "Lewis Acid Promoted Decomposition of Unsaturated α-Diazo Ketones: An Efficient Approach to Simple and Annulated Cyclopentenones," *J. Am. Chem. Soc.* (1981) 103:1996-2008.

Sommerfeldt et al., "Metabolism of Orally Administered [$^3$H]Ergocalciferol and [$^3$H]Cholecalciferol by Dairy Calves," *J. Nutr.*, (1983) 11:2595-2600.

Song, XD et al., "Bryostatin-1 and 1 α,25-Dihydroxyvitamin $D_3$ Synergistically Stimulate the Differentiation of NB4 Acute Promyelocytic Leukemia Cells," *Leukemia* (1999) 13:275-281.

Sorensen, O.H. et al., "Treatment of Senile Osteoporosis with 1α-Hydroxyvitamin $D_3$," *Clin. Endocrinol.*, (1977) 7:169S-175S.

Strugnell et al., "Metabolism of a Cyclopropane-Ring-Containing Analog of 1α-Hydroxyvitamin $D_3$ in a Hepatocyte Cell Model," *Biochem. Pharm.*, (1990) 40:333-341.

Strugnell et al., "1 α,24(S)-Dihydroxyvitamin $D_2$: a biologically active product of 1 α-hydroxyvitamin $D_2$ made in the human hepatoma, Hep3B," *Biochem. J.*, (1995) 310:233-241.

Studzinski, G. et al., "Potentiation by 1-α,25-Dihydroxyvitamin $D_3$ of Cytotoxicity of HL-60 Cells Produced by Cytarabine and Hydroxyurea," *J. Nat. Can. Inst.* (1986)76:4:641-648.

Suzuki, Y. et al., "The Enhancement of the Chemotherapeutic Effects on Human Prostate Cancer Cell—The Combination with the Growth Factor Interaction Inhibitor (Suramin)," *Acta Urologica* (1993) 12:1215-1220, (Abstract).

Swami, S. et al., "1α,25-Dihydroxyvitamin $D_3$ Down-Regulates Estrogen Receptor Abundance and Suppresses Estrogen Action sin MCF-7 Human Breast Cancer Cells," *Clin. Cancer Res.* (2000) 6:3371-3379.

Tachibana, Y. (Nisshin Flour Milling Co.), "Preparation of 1Beta-Hydroxyvitamin $D_2$ and $D_3$," *CHEMICAL ABSTRACTS*, (1990) 113:1:6688 Col. 2 Abstract No. 6683y.

Tanaka, Y. et al., "Biological Activity of 1,25-Dihydroxyvitamin $D_3$ in the Rat," *Endocrinology* (1973) 92:417-422.

Torres, R. et al., "Etoposide Stimulates 1,25-Dihydroxyvitamin $D_3$ Differentiation Activity, Hormone Binding and Hormone Receptor ExpressioninHL-60 Human Promyelocytic Cells," *Molecular & Cellular Biochem.* (2000) 208:157-162.

Tsuji, M. et al., "Synthesis of 22,23-Dihydro-1α,25-Dihydroxyvitamin $D_2$ and its 24R-Epimer, New Vitamin $D_2$ Derivatives," *Bull. Chem. Soc. Jpn.*, (1990) 63:8:2233-2238.

Walba D. et al., "A Highly Stereocontrolled Route to the Monensin Spiroketal Ring System," *J. Org. Chem.* (1988) 53:1046-1056.

Wang, Q. et al., "1,25-Dihydroxyvitamin $D_3$ and All-trans-Retinoic Acid Sensitize Breast Cancer Cells to Chemotherapy-induced Cell Death," *Cancer Research*, (Apr. 2000) 60:2040-2048.

Wang, X. et al., "Inhibition of p38 MAP Kinase Activity Up-Regulates Multiple MAP Kinase Pathways and Potentiates 1,25-Dihydroxyvitamin $D_3$—Induced Differentiation of Human Leukemia HL60 Cells," *Experimantal Cell Research*, (2000) 258:425-437.

Welsh J., "Induction of Apoptosis in Breast Cancer Cells in Response to Vitamin D and Antriestrogens," *Biochem. Cell. Biol.* (1994) 72:11-12:537-545.

White, J. et al., "Total Synthesis of (−)-$C_{34}$-Botryococcene, the Principal Triterpenoid Hydrocarbon of the Freshwater Alga *Botryococcus braunli*," *Chem. Soc. Perkin Trans.* (1993) 759-767.

Wientroub, S. et al. "The Dichotomy in the Effects of 1,25 Dihydroxy Vitamin $D_3$ and 24, 25 Dihydroxy Vitamin $D_3$ on Bone Gamma-Carboxyglutamic Acid-Containing Protein in Serum and Bone in Vitamin D-Deficient Rats," *Calcif. Tissue Int.*, (1987) 40:166-172.

Wigington, D. et al., "Combination Study of 1,24(S)-Dihydroxyvitamin D2 and Chemotherapeutic Agents on Human Breast and Prostate Cancer Cell Lines," *Anticancer Research*, (2004) 24:2905-2912.

Windaus, A. et al., "Uber das Krystallisierte Vitamin $D_4$," *Z. Physiol. Chem.*, (1937) 247:185-188.

Yu, W. et al., "Enhancement of 1,25- Dihydroxyvitamin $D_3$-Mediated Antitumor Activity with Dexamethasone," *J. National Cancer Inst.*, (Jan. 1998) 90:2:134-141.

Zerwekh et al., "Short-Term 1,25-Dihydroxyvitamin $D_3$ Administration Raises Serum Osteocalcin in Patients with Postmenopausal Osteoporosis," *J. Clin. Endocrinol. Metabol*, (1985) 60:615-617.

* cited by examiner

Combination Index (CI) values for chemotherapeutic drugs and $1,24(OH)_2D_2$ combinations in MCF-7 cells.

| Drug | Drug Concentration | $1,24(OH)_2D_2$ Concentration | Drug / $1,24(OH)_2D_2$ Molar Ratio | Combination Index (Mean ± S.E.M.) | p value | Interaction |
|---|---|---|---|---|---|---|
| Busulfan | 30.1 μM | 0.1 nM | $3.0 \times 10^5$ | 0.97 ± 0.12 | 0.817 | Additive |
|  | 23.2 μM | 1.0 nM | $2.3 \times 10^4$ | 0.88 ± 0.14 | 0.506 | Additive |
|  | 17.6 μM | 10 nM | $1.8 \times 10^3$ | 1.35 ± 0.47 | 0.539 | Additive |
| Carboplatin | 1.9 μg/ml | 0.1 nM | $5.0 \times 10^1$ | 1.03 ± 0.06 | 0.643 | Additive |
|  | 1.8 μg/ml | 1.0 nM | $4.7 \times 10^0$ | 1.03 ± 0.27 | 0.916 | Additive |
|  | 1.4 μg/ml | 10 nM | $3.9 \times 10^{-1}$ | 1.05 ± 0.14 | 0.749 | Additive |
| Cisplatin | 1.5 μg/ml | 0.01 nM | $5.1 \times 10^1$ | 0.68 ± 0.09 | 0.071 | Synergistic |
|  | 1.4 μg/ml | 0.1 nM | $4.5 \times 10^0$ | 0.62 ± 0.11 | 0.052 | Synergistic |
|  | 1.5 μg/ml | 1.0 nM | $5.1 \times 10^{-1}$ | 0.69 ± 0.01 | 0.002 | Synergistic |
| Chlorambucil | 7.4 μM | 0.1 nM | $7.4 \times 10^4$ | 3.18 ± 0.24 | 0.040 | Antagonistic |
|  | 6.3 μM | 1.0 nM | $6.3 \times 10^3$ | 2.75 ± 0.12 | 0.043 | Antagonistic |
|  | 3.8 μM | 10 nM | $3.8 \times 10^2$ | 2.47 ± 0.08 | 0.032 | Antagonistic |
| Doxorubicin | 5.6 ng/ml | 0.01 nM | $9.7 \times 10^{-1}$ | 0.48 ± 0.13 | 0.057 | Synergistic |
|  | 7.2 ng/ml | 0.1 nM | $1.2 \times 10^{-1}$ | 0.64 ± 0.09 | 0.058 | Synergistic |
|  | 5.6 ng/ml | 1.0 nM | $9.6 \times 10^{-3}$ | 0.51 ± 0.02 | 0.001 | Synergistic |
|  | 1.9 ng/ml | 10 nM | $3.2 \times 10^{-4}$ | 0.41 ± 0.04 | 0.005 | Synergistic |
| Etoposide | 0.45 μM | 0.1 nM | $4.5 \times 10^3$ | 1.66 ± 0.41 | 0.251 | Additive |
|  | 0.35 μM | 1.0 nM | $3.5 \times 10^2$ | 1.31 ± 0.48 | 0.583 | Additive |
|  | 0.09 μM | 10 nM | $8.8 \times 10^0$ | 0.70 ± 0.21 | 0.284 | Additive |
| 5-Fluorouracil | 0.99 μM | 0.1 nM | $9.9 \times 10^3$ | 1.73 ± 0.25 | 0.100 | Additive |
|  | 0.98 μM | 1.0 nM | $9.8 \times 10^2$ | 1.89 ± 0.56 | 0.252 | Additive |
|  | 0.39 μM | 10 nM | $3.9 \times 10^1$ | 1.28 ± 0.10 | 0.140 | Additive |
| Tamoxifen | 2.9 μM | 0.01 nM | $2.9 \times 10^5$ | 1.48 ± 0.20 | 0.141 | Additive |
|  | 2.2 μM | 0.1 nM | $2.2 \times 10^4$ | 1.07 ± 0.36 | 0.866 | Additive |
|  | 3.3 μM | 1.0 nM | $3.2 \times 10^3$ | 1.92 ± 0.81 | 0.373 | Additive |
| Paclitaxel * | 0.79 μM | 0.01 nM | $7.9 \times 10^4$ | 0.53 |  | Synergistic |
|  | 1.0 μM | 0.1 nM | $1.0 \times 10^4$ | 0.68 |  | Synergistic |
|  | 2.0 μM | 1.0 nM | $2.0 \times 10^3$ | 1.43 |  | Mod. Antagonistic |

* Paclitaxel Experiment was only performed once, therefore there is no S.D. or P values for C.I.

FIG. 21

METHOD OF TREATING BREAST CANCER USING A COMBINATION OF VITAMIN D ANALOGUES AND OTHER AGENTS

CROSS-REFERENCE TO RELATED APPLICATIONS

None

TECHNICAL FIELD

This invention relates generally to a method of treating hyperproliferative diseases, particularly breast cancer. The method of the invention uses active compounds of vitamin D in combination with other agents to inhibit the hyperproliferative cellular activity of these diseases and to promote differentiation of the cells.

BACKGROUND OF THE INVENTION

Breast cancer is the most commonly diagnosed cancer in women in both United States and worldwide. Breast cancer rates are the highest in industrialized countries. In the United States, the incidence of breast cancer has more than doubled in the past 30 years. In 1964, the lifetime risk was 1 in 20. Today it's 1 in 8. Approximately 185,700 new cases are diagnosed in the U.S. annually, and breast cancer is responsible for about 44,560 deaths in the U.S. per year. An estimated 3 million women in the U.S. today are living with breast cancer of which 2 million have been diagnosed with the disease and 1 million have the disease but do not yet know it. Worldwide, it is estimated that 1.2 million new diagnoses and 500,000 deaths from breast cancer will occur this year.

While predominantly observed in women, 1,400 cases of breast cancer are diagnosed annually in men, and 260 men die of breast cancer per year. When breast cancer does occur in men, it is usually not recognized until late, and thus, the results of treatment are poor. In women, carcinoma of the breast is rarely seen before the age of 30 and the incidence rises rapidly after menopause.

Breast cancer often first manifests itself as a painless lump, detectable by self-examination and clinical breast exams including mammograms. Commonly, growth initiates in the lining of the ducts or in the lobules of the breast.

No universally successful method for the prevention or treatment of breast cancer is currently available. Management of the disease currently relies on a combination of early diagnosis (through routine breast screening procedures) and aggressive treatment, which may include one or more of surgery, radiotherapy, chemotherapy and hormone therapy. Current surgical treatments include mastectomy (removal of the entire breast) or lumpectomy (removal of the tumor and surrounding tissue) for localized tumors. Localized disease can be effectively treated by surgery, if all of the cancer can be removed. Surgical treatment is often followed by chemotherapy, radiotherapy, or hormone-blocking therapy, especially if the disease has metastasized. Breast cancer cells can metastasize to the lymph nodes, skin, lungs, liver, brain, or bones. Metastasis may occur early or late in the disease progression, although typically metastasis occurs once the cancerous growth reaches a size of about 20 mm. Currently, there are no therapies that are effective for long term treatment of breast cancer that has metastasized to lymph nodes or distal sites.

It has been reported that certain vitamin D compounds and analogues are potent inhibitors of malignant cell proliferation and are inducers/stimulators of cell differentiation. For example, U.S. Pat. No. 4,391,802 issued to Suda et al. discloses that 1α-hydroxyvitamin D compounds, specifically 1α,25-dihydroxyvitamin $D_3$ and 1α-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Antiproliferative and differentiating actions of 1α,25-dihydroxyvitamin $D_3$ and other vitamin $D_3$ analogues have also been reported with respect to cancer cell lines. More recently, an association between vitamin D receptor gene polymorphism and cancer risk has been reported, suggesting that vitamin D receptors may have a role in the development, and possible treatment, of cancer.

Previous studies of vitamin D compounds and cancer treatment have focused exclusively on vitamin $D_3$ compounds. Even though these compounds may indeed be highly effective in promoting differentiation in malignant cells in culture, their practical use in differentiation therapy as anticancer agents is severely limited because of their equally high potency as agents affecting calcium metabolism. At the levels required in vivo for effective use as, for example, antileukemic agents, these same compounds can induce markedly elevated and potentially dangerous blood calcium levels by virtue of their inherent calcemic activity. That is, the clinical use of 1α,25-dihydroxyvitamin $D_3$ and other vitamin $D_3$ analogues as anticancer agents is severely limited by the risk of hypercalcemia. This indicates a need for compounds with greater specific activity and selectivity of action, i.e., vitamin D compounds with antiproliferative and differentiating effects but which have less calcemic activity. It also indicates a need for co-administration agents which can be combined with vitamin $D_3$ agents, allowing for smaller doses of vitamin $D_3$ compounds to be used while achieving the same or greater beneficial effect.

SUMMARY OF THE INVENTION

The present invention includes a method of inhibiting or reducing the hyperproliferative activity of human breast cancer or neoplastic cells. The method includes use of active vitamin D compounds with other anticancer agents to additively or synergistically inhibit abnormal cell growth and/or promote cell differentiation.

It is anticipated that the vitamin D compounds used in combination with various anticancer drugs can give rise to a significantly enhanced cytotoxic or antineoplastic effect on cancerous cells, thus providing an increased therapeutic effect. Specifically, a significantly increased growth-inhibitory effect is obtained with the above disclosed combinations utilizing lower concentrations of the anticancer drugs compared to the treatment regimes in which the drugs are used alone. Such combinations provide therapy wherein adverse side effects associated with the various anticancer drugs are considerably reduced compared to side effects normally observed with the anticancer drugs used alone in larger doses. Alternatively, such combination therapy allows for a greater antineoplastic effect to be derived from the usual dose of anticancer drugs used in standard treatment regimes, enhancing the effectiveness of the therapy and/or reducing the total number of treatments required.

The foregoing are realized in one aspect by providing a pharmaceutical combination comprising a first and second agent. The first agent comprises 1α,24-dihydroxyvitamin $D_2$ and the second agent comprises doxorubicin, cisplatin and paclitaxel or combinations thereof. The first and second agents are suitably present in therapeutically effective amounts and agents work synergistically to inhibit the growth of human breast cancer cells.

The invention also provides a method of synergistically inhibiting the growth of human breast cancer cells. The method comprises contacting the cells with a first composition which comprises 1α,24-dihydroxyvitamin $D_2$ and a second composition which comprises an agent selected from the group consisting of doxorubicin, cisplatin and paclitaxel or combinations thereof.

The invention also provides for a combination of vitamin D agents and anticancer agents that work additively. In this aspect of the invention, a pharmaceutical combination is provided. The pharmaceutical combination comprises a first agent which is 1α,24-dihydroxyvitamin $D_2$ and a second agent which is selected from the group consisting of busulfan, carboplatin, etoposide, 5-fluorouracil and tamoxifen. The first and second agents have additive properties for inhibiting growth of human breast cancer cells.

The invention also provides another pharmaceutical combination for the inhibition of human breast cancer cells. The pharmaceutical combination comprises a therapeutically effective dose of an additive combination of a first agent which is 1α,24-dihydroxyvitamin $D_2$ and a second agent which is selected from the group consisting of busulfan, carboplatin, etoposide, 5-fluorouracil and tamoxifen.

In another embodiment the invention provides a method of additively inhibiting the growth of human breast cancer cells. The method comprises contacting the cells with a first composition which comprises 1α,24-dihydroxyvitamin $D_2$ and a second composition which comprises an agent selected from the group consisting of busulfan, carboplatin, etoposide, 5-fluorouracil and tamoxifen or combinations thereof.

Effective amounts of active vitamin D compounds can be administered to patients with cancer or neoplasms. When administered the proliferative activity of the abnormal neoplastic cells is inhibited, reduced, or stabilized, and/or cell differentiation is induced, promoted or enhanced.

The effective amounts of vitamin D compound can be given in an administration protocol in a variety of dose ranges depending on the particular need of the patient. One such suitable dose range is a range from 0.01 μg to 400 μg. Another suitable dose range is administered on a daily basis per kilogram of body weight, the dose ranges being from 0.001 μg/kg/day to 5.0 μg/kg/day. Another dosing regimen calls for a high dosage, generally 10 μg/dose or greater up to 400 μg/dose or greater, given episodically or intermittently. The protocol or dosage regimen in accordance with the present invention provides an improved therapeutic index for active forms of vitamin D analogues compared to administration via conventional regimens. The episodic dosing is also cost effective as a lower quantity of active agent is needed.

Administration of the active vitamin D may be prior to, simultaneous with, or after administration of the other therapeutic agents.

All routes of administration of the active vitamin D or its co-administration with other therapeutic agents are suitable. However, parenteral administration of the active vitamin D compounds alone or in combination with other agents, provides advantages over other treatment modalities. Parenteral administration bypasses the increased calcemic activity that occurs in the gastrointestinal tract from oral administration and reduces incidence or risk of esophagitis. Parenteral dosing also provides for greater compliance and safety because the drugs are generally administered by a health care professional.

A fuller appreciation of specific adaptations, compositional variations, and physical attributes will be gained upon an examination of the following detailed description of preferred embodiments, taken in conjunction with the appended claims.

BRIEF DESCRIPTION OF THE DRAWING(S)

FIG. 21 shows combination index values for chemotherapeutic agents and 1α,24-dihydroxyvitamin $D_2$ combinations in MCF-7 cells.

Figure 1:
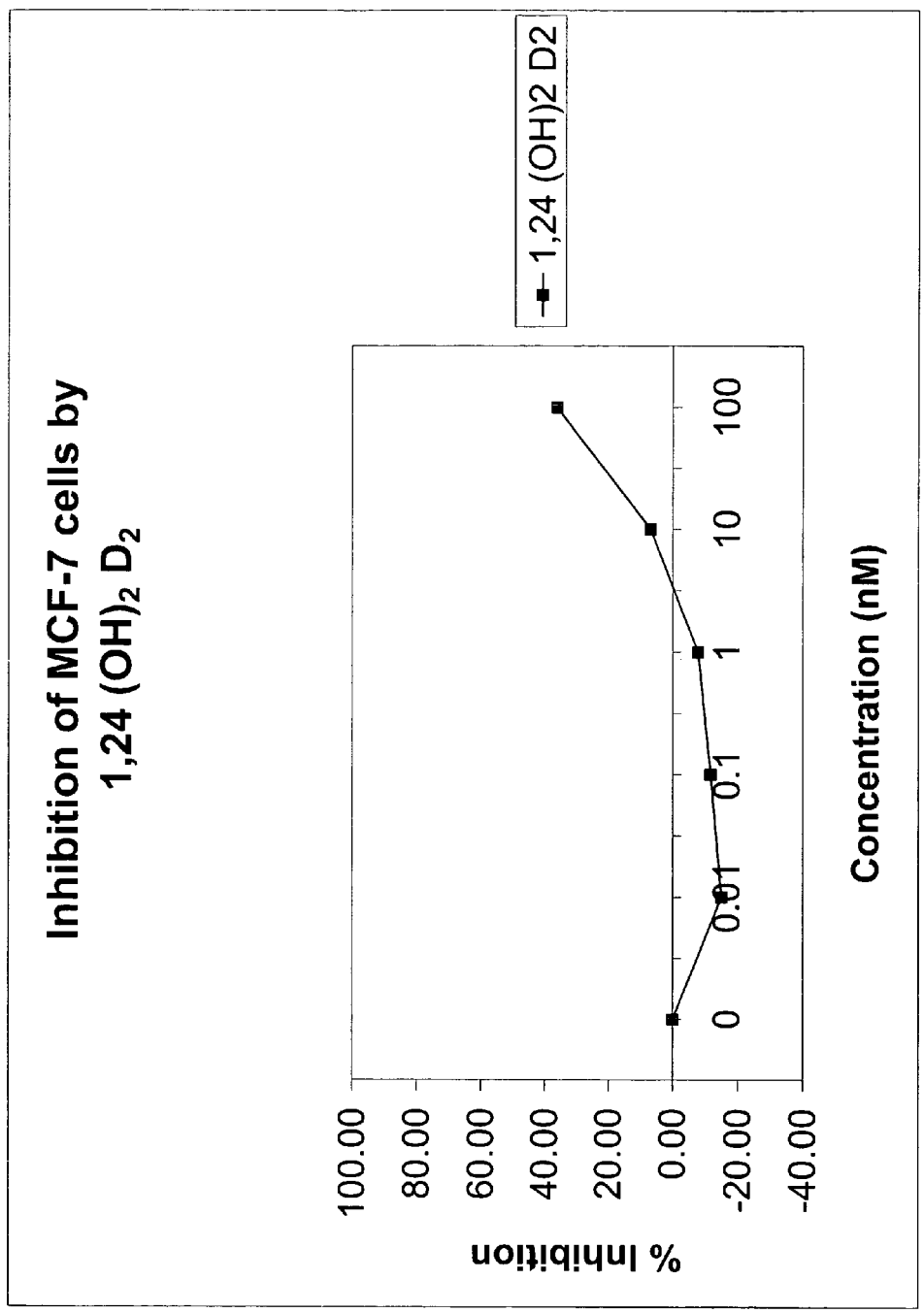
FIG. 1 shows the growth inhibition of MCF-7 cells by 1α,24-dihydroxyvitamin $D_2$.

Before the embodiments of the invention are explained in detail, it is to be understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION OF THE INVENTION

The present invention includes an effective method for the treatment of neoplastic and hyperplastic diseases. Particularly, the present invention relates to therapeutic methods for inhibiting, ameliorating or alleviating the hyperproliferative cellular activity of diseases of the breast, e.g., breast cancer, and inducing, enhancing or promoting cell differentiation in the diseased cells. The present invention includes a method of inhibiting or reducing the hyperproliferative activity of human breast cancer cells. The method includes use of active vitamin D compounds with other anticancer agents to additively or synergistically inhibit abnormal cell growth and/or promote cell differentiation. Suitably, the active vitamin D analogs is $1\alpha,24$-dihydroxyvitmin $D_2$.

As used herein the term "additively inhibits" means that the total inhibitory effect of the agents administered is approximately the sum of their individual inhibitory effects.

As used herein the term "synergistically inhibits" means that the total inhibitory effect of the agents administered is greater than the sum of the individual inhibitory effects of the agents.

It is known that vitamin $D_3$ must be hydroxylated in the C-1 and C-25 positions before it is activated, i.e., before it will produce a biological response. A similar metabolism appears to be required to activate other forms of vitamin D, e.g., vitamin $D_2$ and vitamin $D_4$. Therefore, as used herein, the term "activated vitamin D" or "active vitamin D" is intended to refer to a vitamin D compound or analogue that has been hydroxylated in at least the C-1 position of the A ring of the molecule and either the compound itself or its metabolites in the case of a prodrug, such as $1\alpha$-hydroxyvitamin $D_2$, binds the vitamin D receptor (VDR). Vitamin D compounds which are hydroxylated only in the C-1 position are referred to herein as "prodrugs." Such compounds undergo further hydroxylation in vivo and their metabolites bind the VDR.

Also, as used herein, the term "lower" as a modifier for alkyl, alkenyl acyl, or cycloalkyl is meant to refer to a straight or branched, saturated or unsaturated hydrocarbon radical having 1 to 4 carbon atoms. Specific examples of such hydrocarbon radicals are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. The term "aromatic acyl" is meant to refer to a unsubstituted or substituted benzoyl group.

As used herein, the term "hydrocarbon moiety" refers to a lower alkyl, a lower alkenyl, a lower acyl group or a lower cycloalkyl, i.e., a straight or branched, saturated or unsaturated $C_1$–$C_4$ hydrocarbon radical.

The term "contacting" is used herein interchangeably with the following: combined with, added to, mixed with, passed over, incubated with etc. Moreover, the compounds of present invention can be "administered" by any conventional method such as, for example, parenteral, oral, topical and inhalation routes as described herein.

Thus, the present invention includes a method of treating malignant breast cells (i.e., inhibiting or reducing their hyperproliferative activity and/or inducing and enhancing their differentiation) with an effective amount of a vitamin D analog, co-administered with various inhibitory agents such that the combination of the vitamin D analog and inhibitory agent provides additive or synergistic effects in the inhibition of hyperproliferative activity of the breast cancer cells, i.e., the cells are treated or contacted with both agents.

The term "co-administration" is meant to refer to a combination therapy by any administration route in which two or more agents are administered to cells, to a patient or to a subject. Co-administration of agents may be referred to as combination therapy or combination treatment. In regard to treatment of patients, the agents may be the same dosage formulations or separate formulations. For combination treatment with more than one active agent, where the active agents are in separate dosage formulations, the active agents can be administered concurrently, or they each can be administered at separately staggered times. The agents may be administered simultaneously or sequentially, as long as they are given in a manner sufficient to allow both agents to achieve effective concentrations in the body. The agents may be administered by different routes, e.g., one agent may be administered intravenously while a second agent is administered intramuscularly, intravenously or orally. The agents also may be in an admixture, as, for example, in a single tablet.

In time-sequential co-administration, one agent may directly follow administration of the other or the agents may be give episodically, i.e., one can be given at one time followed by the other at a later time, e.g., within a week. An example of a suitable co-administration regimen is where an active vitamin D compound is administered from 0.5 to 7 days prior to administration of a cytotoxic or other therapeutic agent.

Use of an active vitamin D analog in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered second anticancer agents are found below in Table 1

TABLE 1

| Agent | Dose Ranges per Day |
|---|---|
| Busulfan | 0.01–0.1 mg/kg |
| Carboplatin | 7.8 mg/kg |
| Cisplatin | 0.4–2.6 mg/kg |
| Chlorambucil | 0.1–0.4 mg/kg |
| Daunomycin | 0.65–1.0 mg/kg |
| Doxorubicin (Adriamycin) | 1.3–1.6 mg/kg |
| Estramustine (Emcyt) | 14 mg/kg |
| Etoposide | 0.75–2.2 mg/kg |
| 5-Fluorouracil | 10–25 mg/kg |
| Hydroxyurea | 20–80 mg/kg |
| Hydroxycarbamide (Hydrea) | 7 mg/kg |
| Idarubicin | 0.26 mg/kg |
| Melphalan (Alkeran) | 0.08–0.2 mg/kg |
| Methotrexate | 0.03–260 mg/kg |
| Mitomycin | 0.1–0.5 mg/kg |
| Paclitaxel | 2.9–3.8 mg/kg |
| Prednimustine | 2.15 mg/kg |
| Tamoxifen | 0.14 mg/kg |

Depending on the combination of the particular vitamin D analog and second anticancer agent, and other factors such as concentration and amount of the agents, additive, synergistic or antagonistic inhibiting growth effects on human breast cancer cells can be found.

1α,24-dihydroxyvitamin $D_2$ when utilized in combination with the agent doxorubicin, cisplatin and paclitaxel can synergistically inhibits the growth of human breast cancer cells. 1α,24-dihydroxyvitamin $D_2$ can also be utilized with a second composition to additively inhibit the growth of human breast cancer cells. Such second compositions include busulfan, carboplatin, etoposide, 5-fluorouracil and tamoxifen and combinations thereof.

The effective amounts of vitamin D compound can be given in an administration protocol in a variety of dose ranges depending on the particular need of the patient. One such suitable dose range is administered on a daily basis per kilogram of body weight, the dose ranges being from 0.001 μg/kg/day to 5.0 μg/kg/day. Another dosing regimen calls for a high dosage, generally 10 μg/dose or greater up to 400 μg/dose or greater, given episodically or intermittently. Such protocols or dosage regimens provide an improved therapeutic index for active forms of vitamin D analogues compared to administration via conventional regimens. The episodic dosing is also cost effective as less active agent is needed.

In an episodic dosing regimen, each single dose is sufficient to upregulate vitamin D hormone receptors in target cells. It is believed that continuous dosing is not required because the binding and upregulation by vitamin D compounds is sufficient to initiate the cascade of intracellular metabolic processes occurring with receptor binding. Intermittent dosing reduces the risk of hypercalcemia, and thus, the method in accordance with the present invention can be used to treat hyperproliferative diseases by administering any active vitamin D compound. At the same time, it is contemplated that the risk of hypercalcemia can be further mitigated if the active vitamin D compound is a hypocalcemic active vitamin D compound.

It is further believed that the intermittent dose regimen can be used to effect any therapeutic effect that is attributable to active vitamin D., e.g., antiproliferative activity, reduction of loss of bone mass, etc. In regard to antiproliferative activity, the value of the intermittent dosing is that antihyperproliferative activity and upregulation of vitamin D receptors occurs with a single dose without the side effects of hypercalcemia and hypercalciuria that occur with recurrent daily dosing.

The episodic dose can be a single dose or, optionally, divided into 2–4 subdoses which, if desired, can be given, e.g., twenty minutes to an hour apart until the total dose is given. The compounds in accordance with the present invention are administered in an amount that raises serum vitamin D levels to a supraphysiological level for a sufficient period of time to induce differentiation or regression of a tumor or neoplasm without causing hypercalcemia or with substantially reduced risk of hypercalcemia. The properties of the hypocalcemic vitamin D compounds are particularly beneficial in permitting such supraphysiologic levels.

As described above, the present invention relates to a method of co-administration of active vitamin D compounds with an anticancer or antineoplastic agent. Therapeutic antihyperproliferative benefits are achieved with intermittent dosing of active vitamin D with cytotoxic, i.e., other chemotherapeutic or antineoplastic, agents. Many antineoplastic or cytotoxic agents must be delivered through a parenteral route of administration, and thus, a protocol of injectable active vitamin D and antineoplastic agent can be set up on a routine basis. The co-administration of active vitamin D and antineoplastic agents can be prior to, after, or simultaneous with each other. However, it is believed that the prior administration of active vitamin D with the later episodic administration of a cytotoxic or antineoplastic agent is of benefit. For example, a high dose active vitamin D upregulates the receptors, and primes and promotes cell differentiation. Such upregulation and priming, potentially permits less cytotoxic or antineoplastic agent than would typically be required if the cytotoxic agent were administered alone.

Those of ordinary skill in the art will readily optimize effective doses and co-administration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of the subject compounds and of a known agent, such as by means of an appropriate conventional pharmacological protocol. A physician of ordinary skill can readily determine and prescribe the effective amount of the drug required to counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. The dosage of active ingredient in the compositions of this invention may be varied; however, it is necessary that the amount of the active ingredient be such that an efficacious dosage is obtained. The active ingredient is administered to patients (animal and human) in need of treatment in dosages that will provide optimal pharmaceutical efficacy.

The active vitamin D analogs and inhibitory agents can be co-administered separately at the same time, at proximate times, or can be delivered simultaneously in an admixture. Both the vitamin D analog, the inhibitory agent, or the admixed combination of the two can be employed in admixtures with conventional excipients, e.g., pharmaceutically acceptable carrier substances suitable for enteral (e.g., oral) or parenteral application which do not deleteriously react with the active compounds.

Active vitamin D compounds can be formulated in pharmaceutical compositions in a conventional manner using one or more conventional excipients, which do not deleteriously react with the active compounds, e.g., pharmaceutically acceptable carrier substances suitable for enteral administration (e.g., oral), parenteral, topical, buccal or rectal application, or by administration by inhalation or insufflation (e.g., either through the mouth or the nose)

Generally, acceptable carriers for pharmaceutical formulation include, but are not limited to, water, salt solutions, alcohols, gum arabic, vegetable oils (e.g., almond oil, corn oil, cottonseed oil, peanut oil, olive oil, coconut oil), mineral oil, fish liver oils, oily esters such as Polysorbate 80, polyethylene glycols, gelatine, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

Of particular interest is the parenteral, e.g., injectable, dosage form. Using the parenteral route of administration allows for bypass of the first pass of active vitamin D compound through the intestine, thus avoiding stimulation of intestinal calcium absorption, and further reduces the risk of esophageal irritation which is often associated with high dose oral administration. Because an injectable route of administration is typically done by a health care professional, the dosing can be more effectively controlled as to precise amount and timing. Parenteral administration suitably includes subcutaneous, intramuscular, or intravenous injection, nasopharyngeal or mucosal absorption, or transdermal absorption. Where indicated, the vitamin D compounds may also be given by direct injection into the tumor by intraarterial delivery or delivery via the portal vein.

The injectable compositions may take such forms as sterile suspensions, solutions, or emulsions in oily vehicles (such as coconut oil, cottonseed oil, sesame oil, peanut oil or soybean oil) or aqueous vehicles, and may contain various formulating agents. Alternatively, the active ingredient may be in powder (lyophilized or non-lyophilized) form for reconstitution at the time of delivery with a suitable vehicle, such as sterile water. In injectable compositions, the carrier is typically sterile, pyrogen-free water, saline, aqueous propylene glycol, or another injectable liquid, e.g., peanut oil for intramuscular injections. Also, various buffering agents, preservatives, suspending, stabilizing or dispensing agents, surface-active agents and the like can be included. Aqueous solutions may be suitably buffered, if necessary, and the liquid diluent first rendered isotonic with sufficient saline or glucose. Aqueous solutions are especially suitable for intravenous, intramuscular, subcutaneous and intraperitoneal injection purposes. In this connection, the sterile aqueous media employed are all readily obtainable by standard techniques well-known to those skilled in the art. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating pathological conditions of the skin, and this may suitably be done by way of creams, jellies, gels, pastes, ointments and the like, in accordance with standard pharmaceutical practice.

The compounds formulated for parenteral administration by injection may be administered, by bolus injection or continuous infusion. Formulations for injection may be conveniently presented in unit dosage form, e.g., in ampoules or in multi-dose, multi-use containers, with an added preservative.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, e.g., a sparingly soluble salt.

Although it is considered that episodic parenteral administration of active vitamin D is highly beneficial, it is also contemplated within the scope of the present invention that enteral dosing, e.g., oral administration, can also be of benefit. Thus, episodic enteral dosing of high dose active vitamin D is also considered of benefit in achieving the upregulation of cell receptors.

For enteral application, particularly suitable are tablets, dragees, liquids, drops, suppositories, lozenges, powders, or capsules. A syrup, elixir, or the like can be used if a sweetened vehicle is desired. For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may also be suitably formulated to give controlled release of the active compound. Many controlled release systems are known in the art.

For buccal administration, the compositions may take the form of tablets, lozenges or absorption wafers formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin, for use in an inhaler or insufflator may be formulated containing a powder mix of the active compound and a suitable powder base such as lactose or starch.

The compounds may also be formulated in rectal or vaginal compositions such as suppositories containing conventional suppository bases or retention enemas. These compositions can be prepared by mixing the active ingredient with a suitable non-irritating excipient which is solid at room temperature (for example, 10° C. to 32° C.) but liquid at the rectal temperature, and will melt in the rectum or vagina to release the active ingredient. Such materials are polyethylene glycols, cocoa butter, other glycerides and wax. To prolong storage life, the composition advantageously may include an antioxidant such as ascorbic acid, butylated hydroxyanisole or hydroquinone.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active compounds, for example, conjugated estrogens or their equivalents, anti-estrogens, calcitonin, bisphosphonates, calcium supplements, cobalamin, pertussis toxin, boron, and antihypercalcemic agents.

The present invention is further explained by the following examples which should not be construed by way of limiting the scope of the present invention.

VDR Binding Analyses

Example 1

1α,24-dihydroxyvitamin $D_2$ [1α,24-$(OH)_2D_2$]

The affinity of 1α,24-$(OH)_2D_2$ for the mammalian vitamin D receptor (VDR) was assessed using a commercially available kit of bovine thymus VDR and standard 1,25-$(OH)_2$ $D_3$ solutions from Incstar (Stillwater, Minn.). The half-maximal binding of chemically synthesized 1α,24-$(OH)_2D_2$ was approximately 150 pg/ml whereas that of 1α,25-$(OH)_2D_3$ was 80 pg/ml. Thus, the 1α,24-$(OH)_2D_2$ had a very similar affinity for bovine thymus VDR as did 1α,25-$(OH)_2D_3$, indicating that 1α,24-$(OH)_2D_2$ has potent biological activity.

Example 2

1α,24-dihydroxyvitamin $D_2$ [1α,24-$(OH)_2D_2$]

VDR binding of vitamin D compounds by breast cells is demonstrated using the techniques of Skowronski et al., 136 *Endocrinology* (1995) 20–26, which is incorporated herein by reference. Breast-derived cell lines are cultured to near confluence, washed and harvested by scraping. Cells are washed by centrifugation, and the cell pellet resuspended in a buffered salt solution containing protease inhibitors. The cells are disrupted by sonication while cooling on ice. The supernatant obtained from centrifuging the disrupted cells at 207,000×g for 35 min at 4° C. is assayed for binding. 200 μL of soluble extract, (1–2 mg protein/ml supernatant) is incubated with a 1 nM 3H-1α,25-$(OH)_2D_3$ and increasing concentrations of 1α,24-$(OH)_2$-$D_2$ (0.01–100 nM) for 16–20 hr at 4° C. Bound and free hormones are separated with hydroxylapatite using standard procedures. Specific binding is calculated by subtracting nonspecific binding obtained in the presence of a 250-fold excess of nonradioactive 1α,25-$(OH)_2D_3$ from the total binding measured. The results demonstrate that 1α,24-$(OH)_2D_2$ has strong affinity for breast VDR, indicating that 1α,24-$(OH)_2D_2$ has potent biological activity in respect of breast cells.

Gene Expression

Example 3

1α,24(S)-dihydroxyvitamin $D_2$ and 1α,24(R)-dihydroxy-vitamin $D_2$ 1α,24(S)-$(OH)_2D_2$ and 1α,24(R)-$(OH)_2D_2$]

Using the plasmids pSG5-hVDR1/3, a vitamin D receptor (VDR)-expressing plasmid, and p(CT4)$_4$TKGH, a plasmid containing a Growth Hormone (GH) gene, under the control of a vitamin D-responsive element (VDRE), experiments were conducted to explore the ability of 1α,24-$(OH)_2D_2$ to induce vitamin D-dependent growth hormone acting as a reporter gene compared to that of 1α,25-$(OH)_2D_3$. Cells in culture were co-transfected into Green monkey kidney, COS-1 cells with these two plasmids. One plasmid contained the gene for Growth Hormone (GH) under the control of the vitamin D responsive element (VDRE) and the other plasmid contained the structural gene for the vitamin D receptor (VDR). These transfected cultures were incubated with 1α,24-$(OH)_2D_2$ or 1α,25-$(OH)_2D_3$, and the production of growth hormone was measured.

As shown in Table 2, both 1α,24(S)-$(OH)_2D_2$ and its epimer, 1α,24(R)-$(OH)_2D_2$, had significantly more activity in this system than 25-OH-$D_3$, with 1α,24(S)-$(OH)_2D_2$ having nearly the same activity as 1α,25-$(OH)_2D_3$.

TABLE 2

Vitamin D-Inducible Growth Hormone Production
In Transfected COS-1 Cells
Vitamin D Inducible Growth Hormone Production

| Inducer | Molar Concentration | Total GH Production* (ng/ml) | Net vitamin D inducible GH-production (ng/ml) |
|---|---|---|---|
| Ethanol | | 44 | 0 |
| 25-OH—$D_3$ | $1 \times 10^{-7}$ | 245 | 201 |
| | $1 \times 10^{-6}$ | 1100 | 1056 |
| | $1 \times 10^{-5}$ | 775 | 731 |
| 1α,25-$(OH)_2D_3$ | $1 \times 10^{-10}$ | 74 | 30 |
| | $1 \times 10^{-9}$ | 925 | 881 |
| | $1 \times 10^{-8}$ | 1475 | 1441 |
| 1α,24(S)—$(OH)_2D_2$ | $5 \times 10^{-10}$ | 425 | 381 |
| | $5 \times 10^{-9}$ | 1350 | 1306 |
| | $5 \times 10^{-8}$ | 1182 | 1138 |
| 1α,24(R)—$(OH)_2D_2$ | $1 \times 10^{-9}$ | 80 | 36 |
| | $1 \times 10^{-8}$ | 1100 | 1056 |
| | $1 \times 10^{-7}$ | 1300 | 1256 |

*Averages of duplicate determinations

Inhibition of Cell Proliferation

Example 4

1α,24-dihydroxyvitamin $D_2$ [1α,24-$(OH)_2D_2$]

Inhibition of cell proliferation is demonstrated using the techniques of Skowronski et al., 132 *Endocrinology* (1993) 1952–1960 and 136 *Endocrinology* (1995) 20–26, both of which are incorporated herein by reference. The cell line MCF-7 is seeded in six-well tissue culture plates at a density of about 50,000 cells/plate. After the cells have attached and stabilized, about 2–3 days, the medium is replenished with medium containing vehicle or the active vitamin D analogue 1α,24-$(OH)_2D_2$, at concentrations from $10^{-11}$ M to $10^{-7}$ M. Medium containing test analogue or vehicle is replaced every three days. After 6–7 days, the medium is removed, the cells are rinsed, precipitated with cold 5% trichloroacetic acid, and washed with cold ethanol. The cells are solubilized with 0.2 N sodium hydroxide, and the amount of DNA determined by standard procedures. The results show that cultures incubated with 1α,24-$(OH)_2D_2$ have significantly fewer cells than the control cultures.

Clinical Studies

Example 5

General Treatment of Cancers with Vitamin D Compounds with Vitamin D Compounds Patients with a known vitamin D receptor positive tumor (e.g., adenocarcinoma of the prostate, breast, lung, colon or pancreas, or transitional cell carcinoma of the bladder, or melanoma) participate in an open-label study of an active vitamin D compound in accordance with the present invention. Patients are placed on a reduced calcium diet prior to treatment, to help minimize intestinal absorption and allow ever higher doses of the active vitamin D. This reduced calcium diet may be continued for the duration of treatment, and for one week after the last dose of the active vitamin D. The diet ideally restricts daily calcium intake to 400–500 mg. Patients also discontinue use of any vitamin D supplements or vitamin D replacement therapies. Each patient is also asked to drink 4–6 cups of fluid more than usual intake to assure adequate oral hydration.

Each subject is monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

A non-daily, episodic dosing regimen is used, e.g., 10 µg or 20 µg per dose to about 200 µg or 400 µg/dose given once a week to once every 12 weeks. The route of administration can vary from oral to intravenous to regional delivery (e.g., arterial infusion, via the portal vein). Oral is typically the easiest route; however, intravenous administration is advantageous for high dosing because, for example, it generally avoids hypercalcemia due to stimulation of calcium absorption in the intestine. Regional delivery also permits high dosing and generally avoids any hypercalcemia. Although, in the case of the hypocalcemic compounds of the present invention, these compounds are inherently of low risk of producing hypercalcemia.

After 18 months of treatment, CAT scans, X-rays and bone scans used for evaluating the progress of metastatic disease show stable disease and partial or complete remission in many patients treated at the high dosage episodic regimen.

Example 6

Treatment of Breast Cancer

The method of Example 5 is used is used to treat patients with breast cancer. After 18 months of treatment, the progress of the cancer shows stable disease or partial remission.

Example 7

1α,24-dihydroxy vitamin $D_2$ [1α,24-$(OH)_2D_2$]

Patients with breast cancer participate in an open-labeled study of 1α,24-$(OH)_2D_2$. Qualified patients are at least 40 years old. On admission to the study, patients begin a course of therapy with oral 1α,24-$(OH)_2D_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral 1α,24-$(OH)_2D_2$ is determined by administering progressively higher dosages to successive groups of patients. All doses are administered in the morning before breakfast. The first group of patients is treated with 25.0 µg of 1α,24-$(OH)_2D_2$. Subsequent groups of patients are treated with 50.0, 75.0 and 100.0 µg/day. Dosing is continued uninterrupted for the duration of the study unless serum calcium exceeds 11.6 mg/dL, or other toxicity of grade 3 or 4 is observed, in which case dosing is held in abeyance until resolution of the observed toxic effect(s) and then resumed at a level which has been decreased by 10.0 µg.

Results from the first phase of the study show that the MTD for 1α,24-$(OH)_2D_2$ is above 20.0 µg/day, a level which is 10- to 40-fold higher than can be achieved with 1α,25-$(OH)_2D_3$. Analysis of blood samples collected at regular intervals from the participating patients reveal that the levels of circulating 1α,24-$(OH)_2D_2$ increase proportionately with the dosage administered, rising to maximum levels well above 100 pg/mL at the highest dosages, and that circulating levels of 1α,25-$(OH)_2D_3$ are suppressed, often to undetectable levels. Serum and urine calcium are elevated in a dose responsive manner. Patients treated with the MTD of 1α,24-$(OH)_2D_2$ for at least six months report that bone pain associated with metastatic disease is significantly diminished.

During the second phase, patients are treated with 1α,24-$(OH)_2D_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

Co-Administration of Vitamin D Analogs and Cytotoxic Agents

Example 8

Co-Administration of Vitamin D Analogs and Cytotoxic Agents Protocol

Vitamin D agents are tested for synergistic and additive interactions with anticancer drugs on human MCF-7 cancer cell lines. MCF-7 cells were plated in 96-well plates in triplicate and allowed to grow 48 hours. The medium was removed and replaced with medium containing vehicle (0.1% Ethanol), vitamin D compound 1,24$(OH)_2D_2$, and/or chemotherapeutic agents (busulfan, 5-fluorouracil, paclitaxel, tamoxifen, cisplatin, carboplatin, doxorubicin, chlorambucil, or etoposide). Cells were allowed to grow for an additional 6 days with media changed on day 3. Cell number was then determined by a colorimetric MTS assay and expressed as a % of change from control cells grown in vehicle only. ID30 values (dose required to inhibit proliferation by 30%) were calculated to compare growth inhibitory effects of the compounds alone and in combination. Isobologram analysis was used to characterize the interaction between vitamin D compounds and anti-cancer drugs as synergistic, additive, or antagonistic.

Example 9

Growth Inhibition of MCF-7 Cells by $1,24(OH)_2D_2$ Alone

MCF-7 cells were plated in 96-well plates in triplicate and allowed to grow 48 hours. The medium was removed and replaced with medium containing vehicle (0.1% Ethanol) and $1,24(OH)_2D_2$ in various concentrations. Cells were allowed to grow for an additional 6 days with media changed on day 3. Cell number was then determined by a calorimetric MTS assay and expressed as a % of change from control cells grown in vehicle only. The growth inhibition of the cells by $1,24(OH)_2D_2$ are shown in FIG. 1.

Example 10

Growth Inhibition of MCF-7 Cells by Etoposide and with $1,24(OH)_2D_2$

Figure 2:
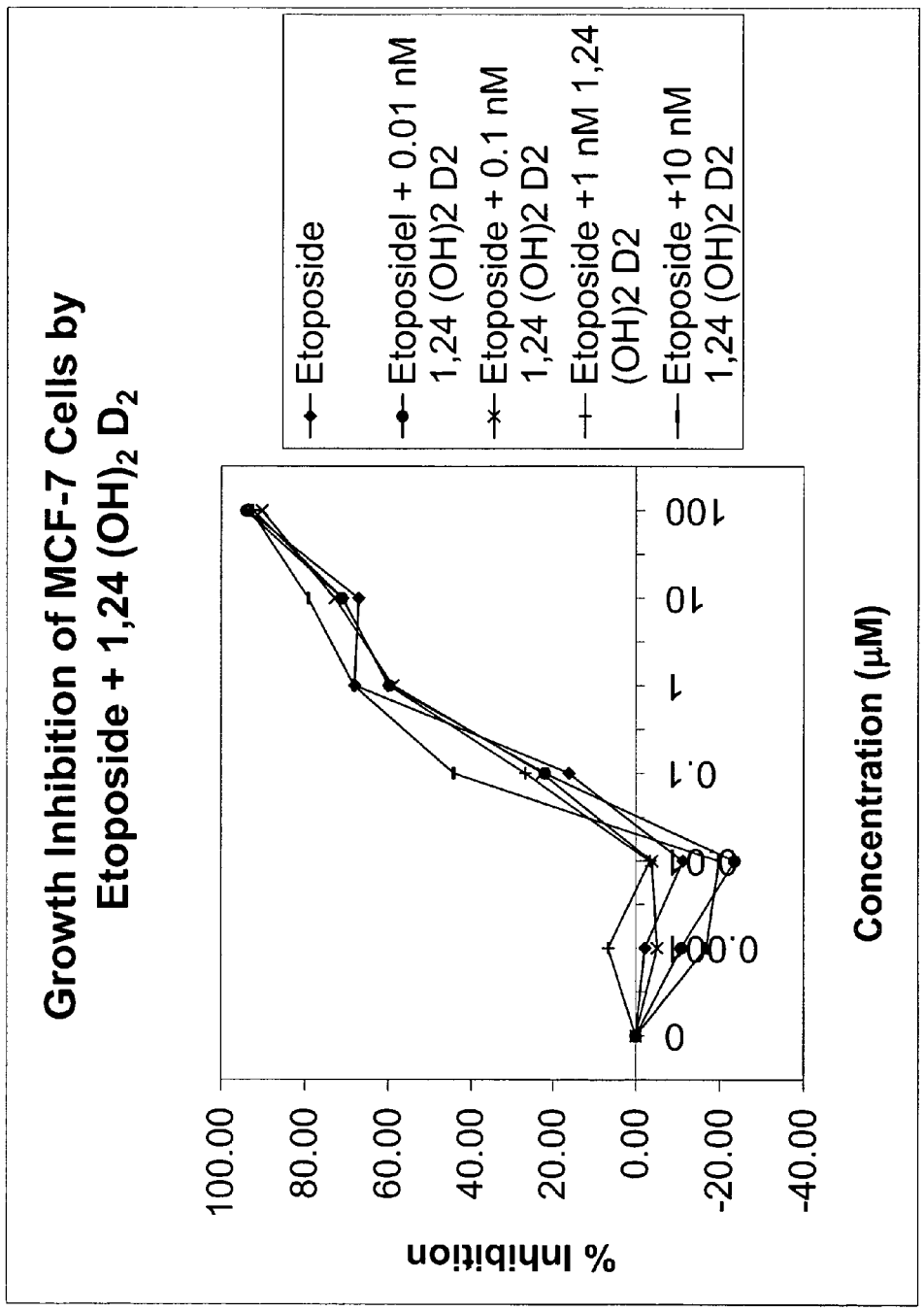
FIG. 2 shows the growth inhibition of MCF-7 cells by etoposide and 1α,24-dihydroxyvitamin $D_2$.
Figure 3:
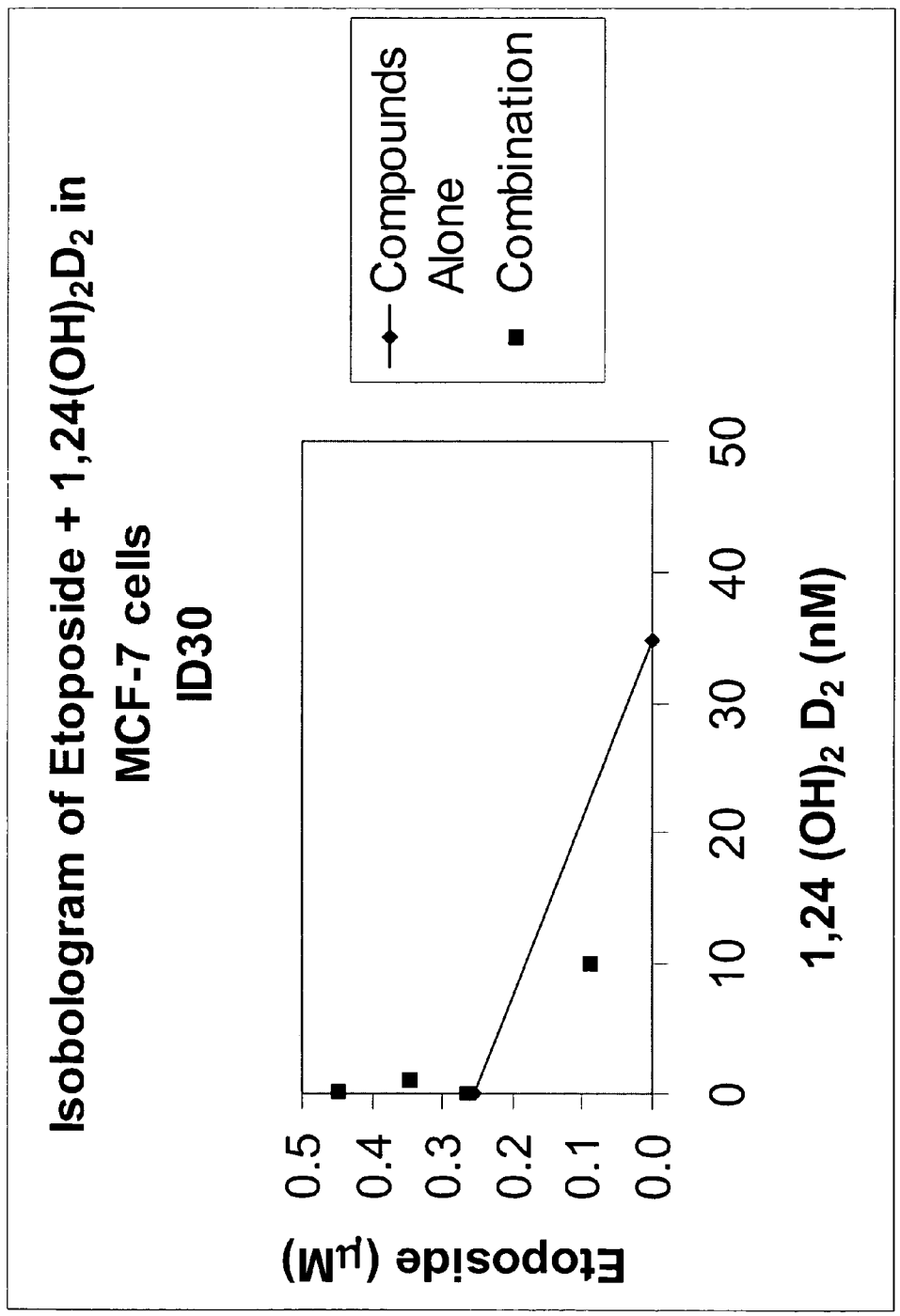
FIG. 3 shows an isobologram of etoposide and 1α,24-dihydroxyvitamin $D_2$ in MCF-7 cells.
Figure 4:
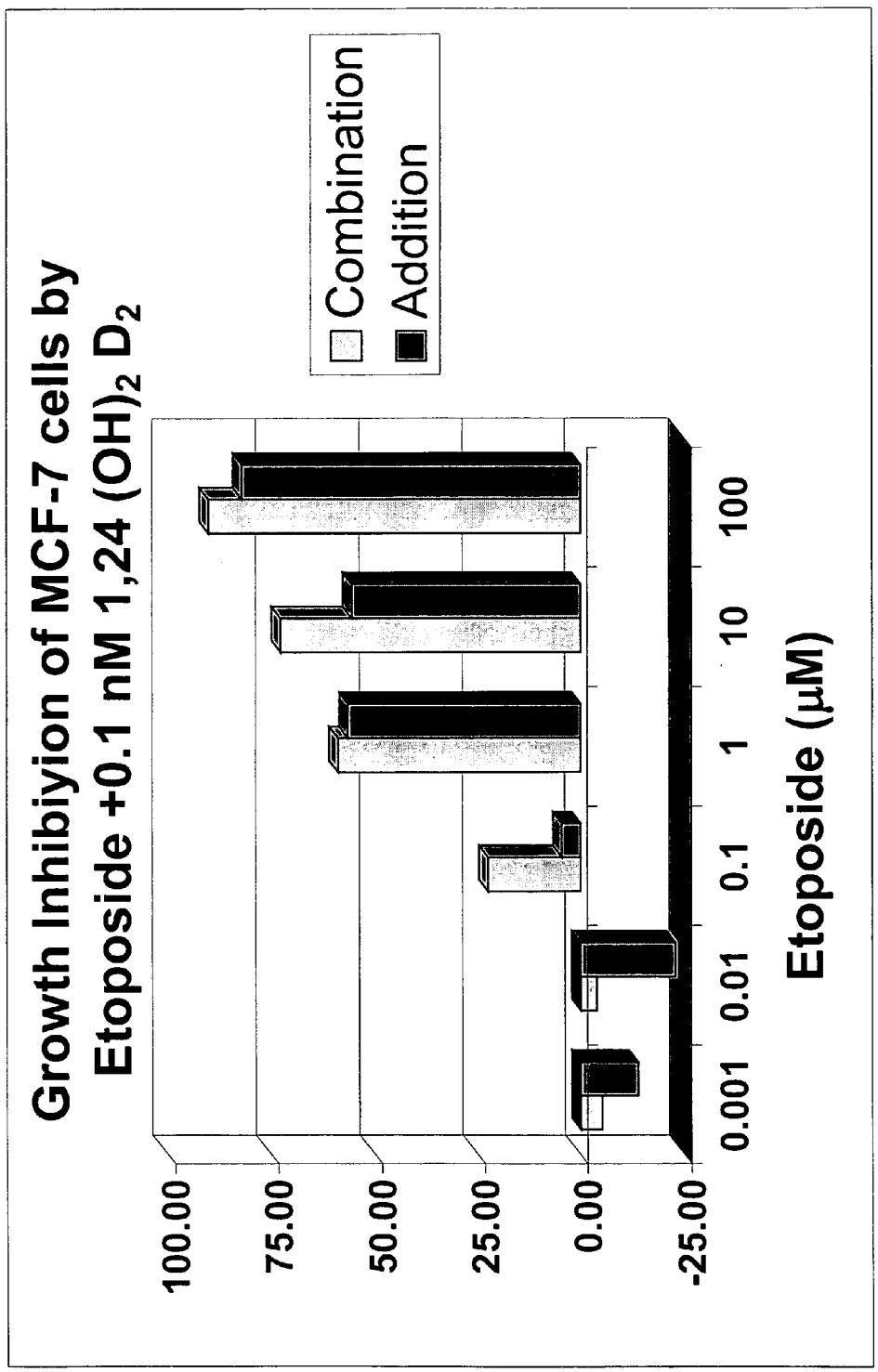
FIG. 4 shows the growth inhibition of MCF-7 cells by etoposide and 0.1 nM 1α,24-dihydroxyvitamin $D_2$.

MCF-7 cells were plated in 96-well plates in triplicate and allowed to grow 48 hours. The medium was removed and replaced with medium containing vehicle (Ethanol), $1,24(OH)_2D_2$ in various concentrations, and etoposide in various concentrations. Cells were allowed to grow for an additional 6 days with media changed on day 3. Cell number was then determined by a calorimetric MTS assay and expressed as a % of change from control cells grown in vehicle only. FIG. 2 shows the percent inhibition of MCF-7 cells of etoposide alone or in combination with various concentrations of $1,24(OH)_2D_2$. ID30 values (dose required to inhibit proliferation by 30%) were calculated to compare growth inhibitory effects of the compounds alone and in combination. Isobologram analysis was used to characterize the interaction between $1,24(OH)_2D_2$ and etoposide as synergistic, additive, or antagonistic. The isobologram is shown in FIG. 3, and shows that etoposide in the concentration range of about 0 to 0.2 µM when combined with $1,24(OH)_2D_2$ of various concentrations can provide an additive or mild synergistic effect. This effect can also be seen in FIG. 4. In FIG. 4 the addition columns show the amount of inhibition predicted if the combination of etoposide and $1,24(OH)_2D_2$ simply had an additive effect on each other. The growth inhibition chart of FIG. 4 shows that the combination of etoposide in concentrations of 0.1 µM, 1 µM, 10 µM and 100 µM with 0.1 nM of $1,24(OH)_2D_2$ produces additive to mild synergistic growth inhibition.

Example 11

Growth Inhibition of MCF-7 Cells by Doxorubicin and with $1,24(OH)_2D_2$

Figure 5:
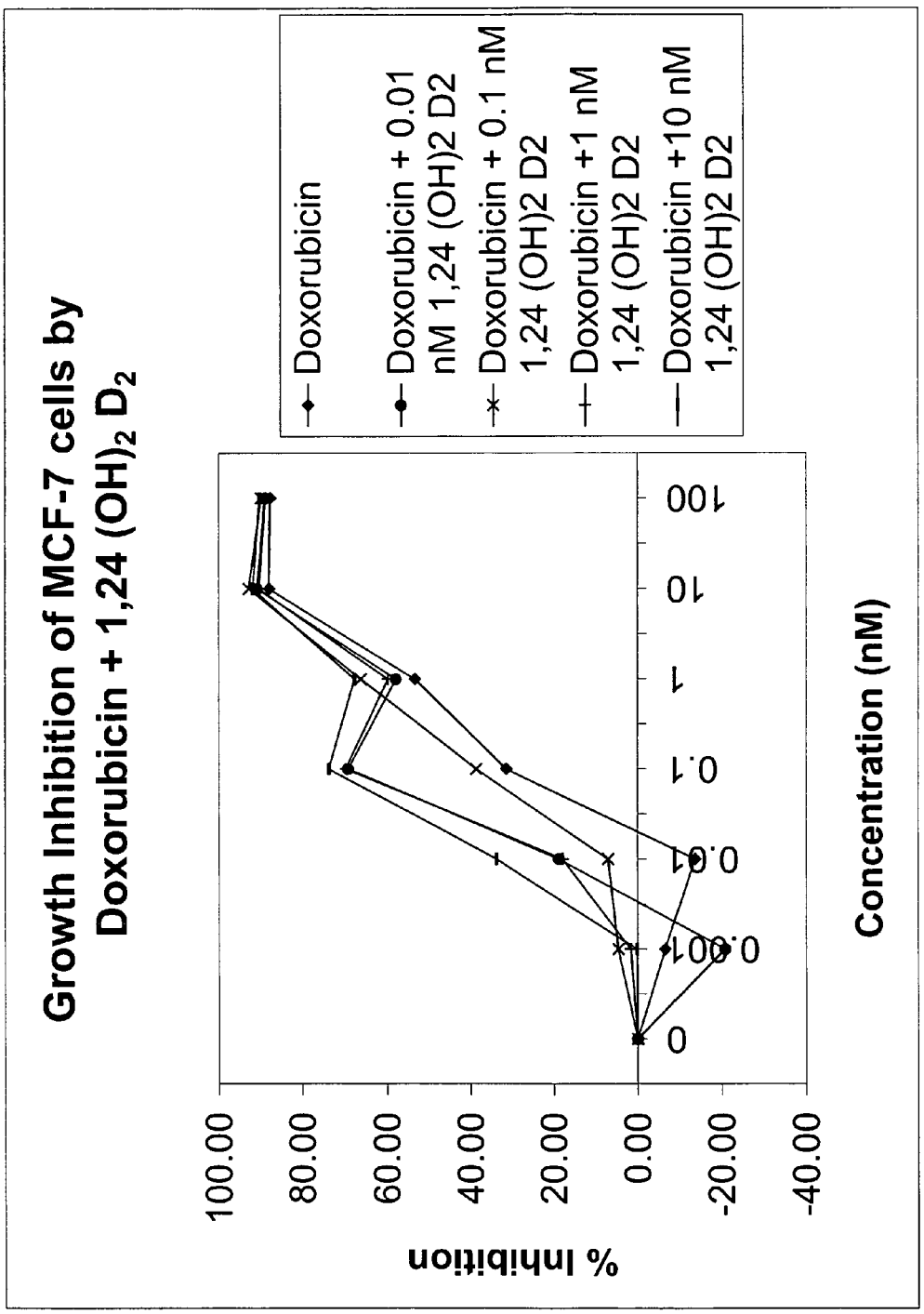
FIG. 5 shows the growth inhibition of MCF-7 cells by doxorubicin and 1α,24-dihydroxyvitamin $D_2$.
Figure 6:
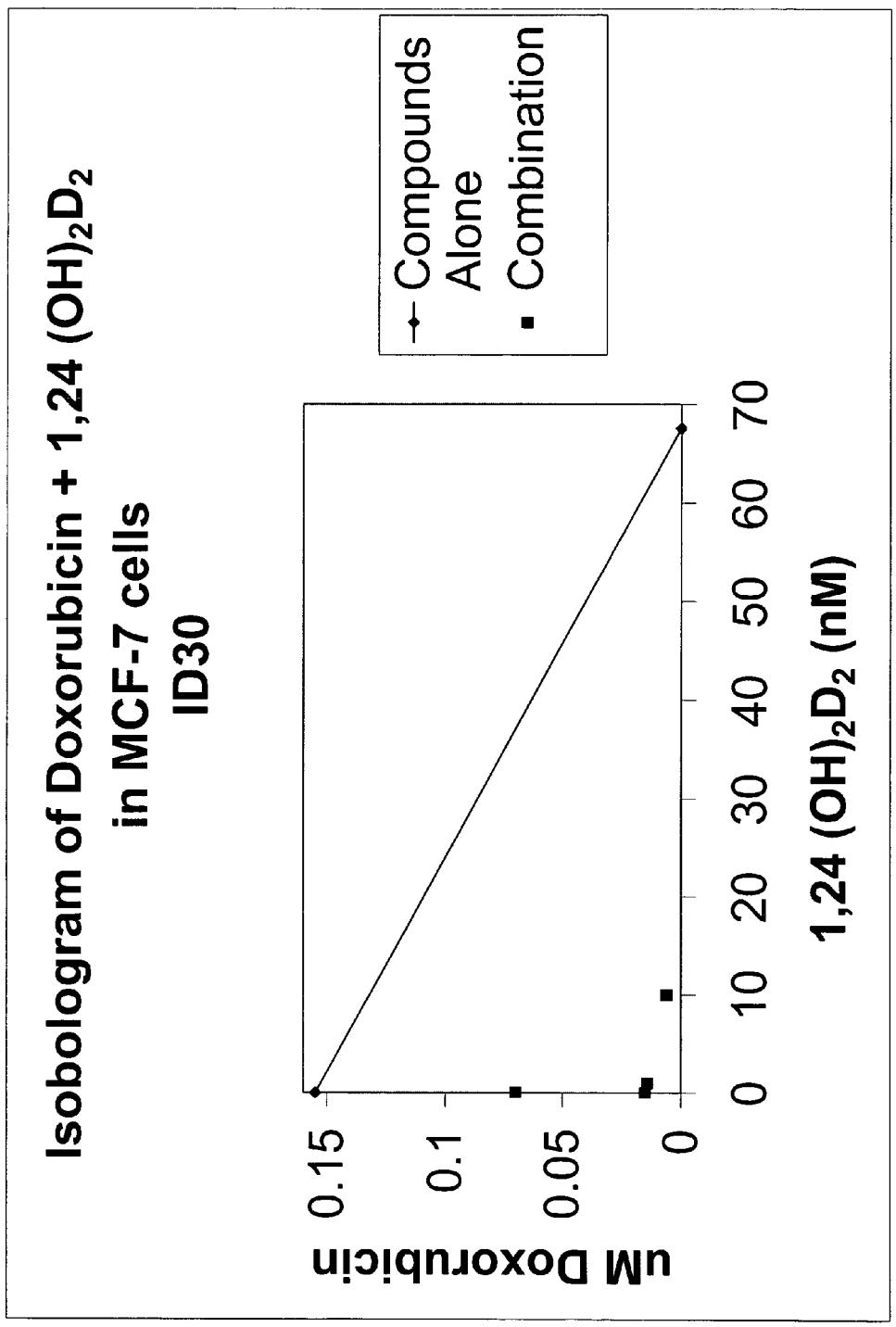
FIG. 6 shows an isobologram of doxorubicin and 1α,24-dihydroxyvitamin $D_2$ in MCF-7 cells.
Figure 7:
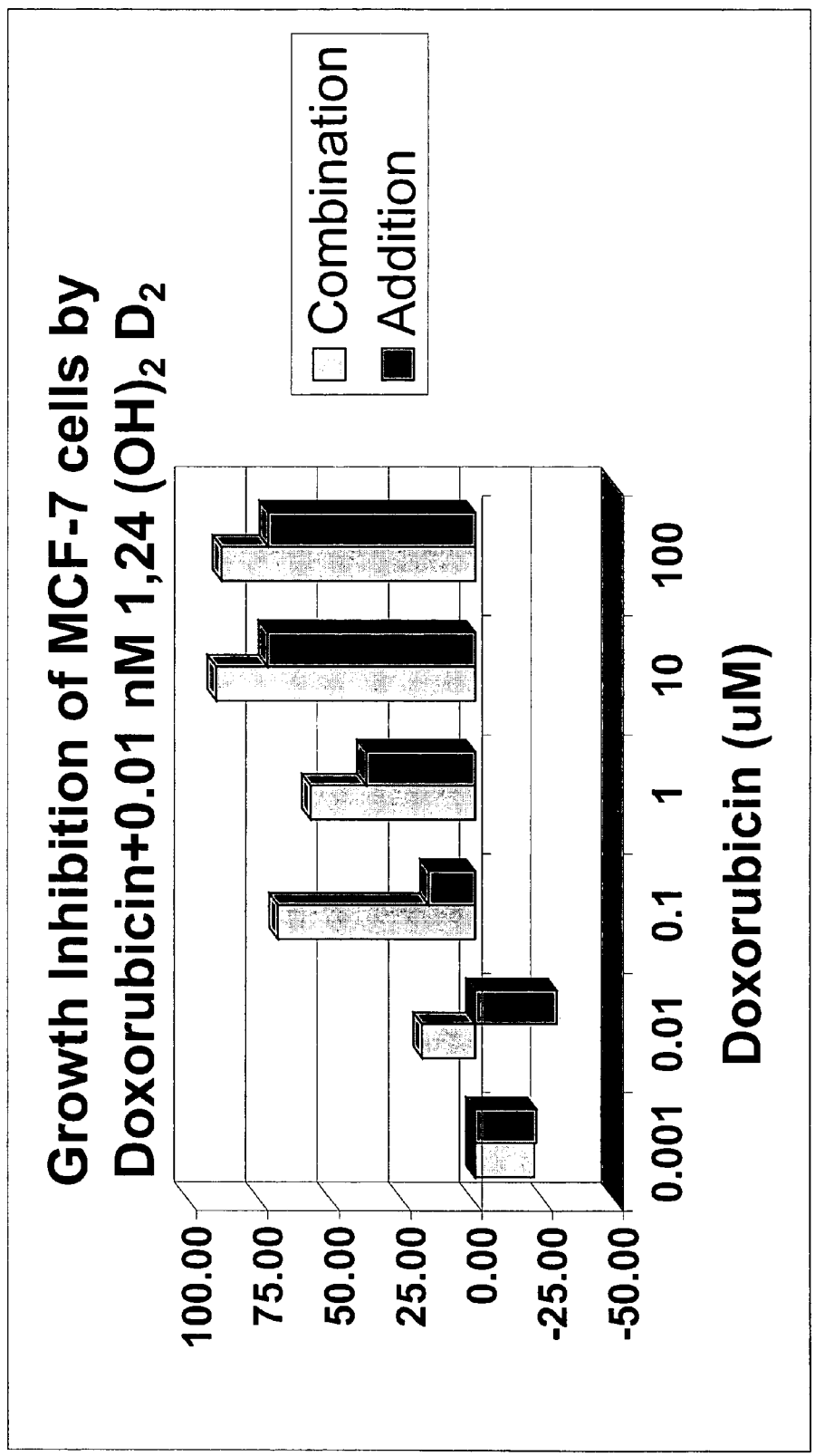
FIG. 7 shows the growth inhibition of MCF-7 cells by doxorubicin and 0.01 nM 1α,24-dihydroxyvitamin $D_2$.
Figure 8:
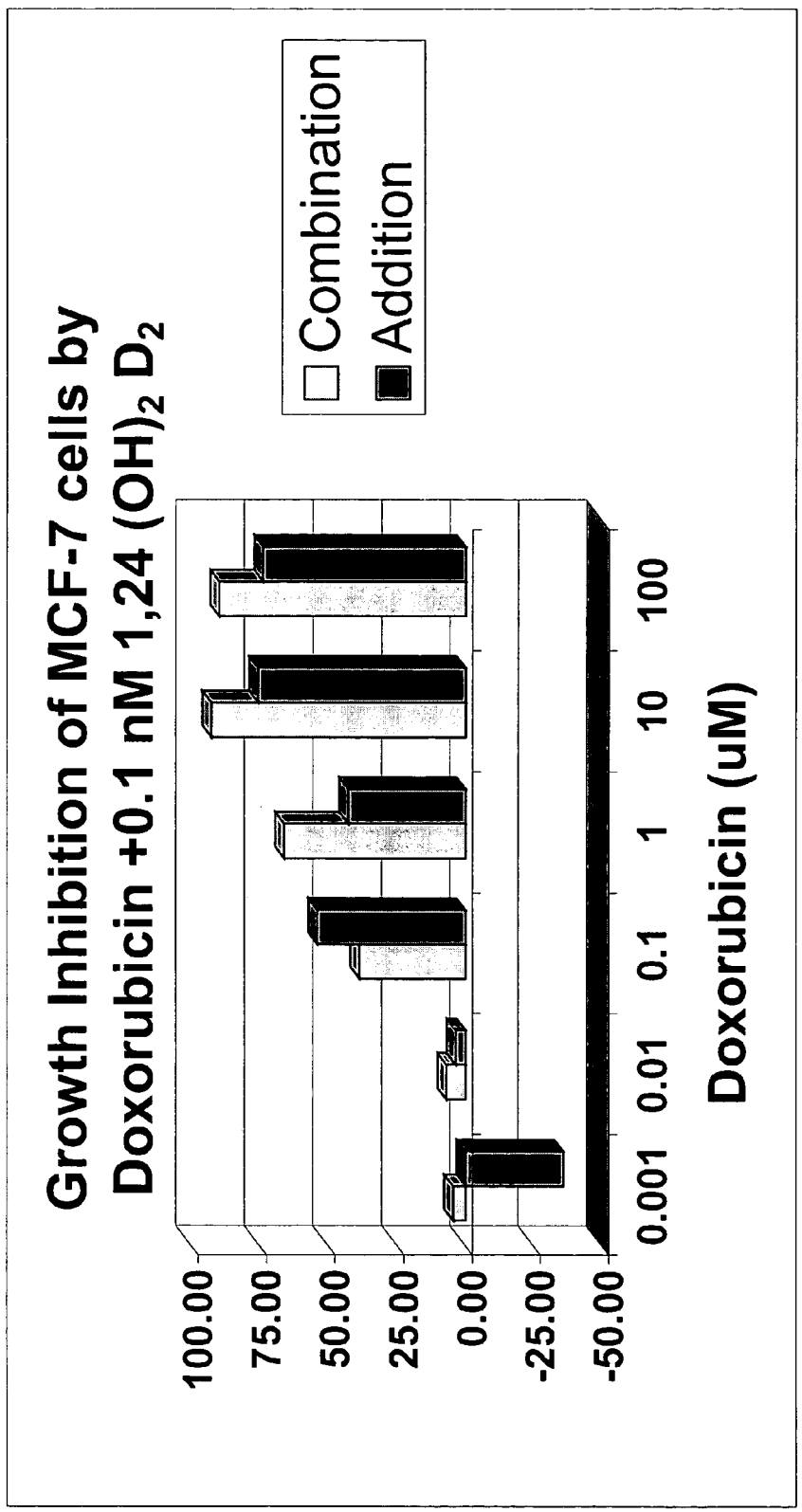
FIG. 8 shows the growth inhibition of MCF-7 cells by doxorubicin and 0.1 nM 1α,24-dihydroxyvitamin $D_2$.
Figure 9:
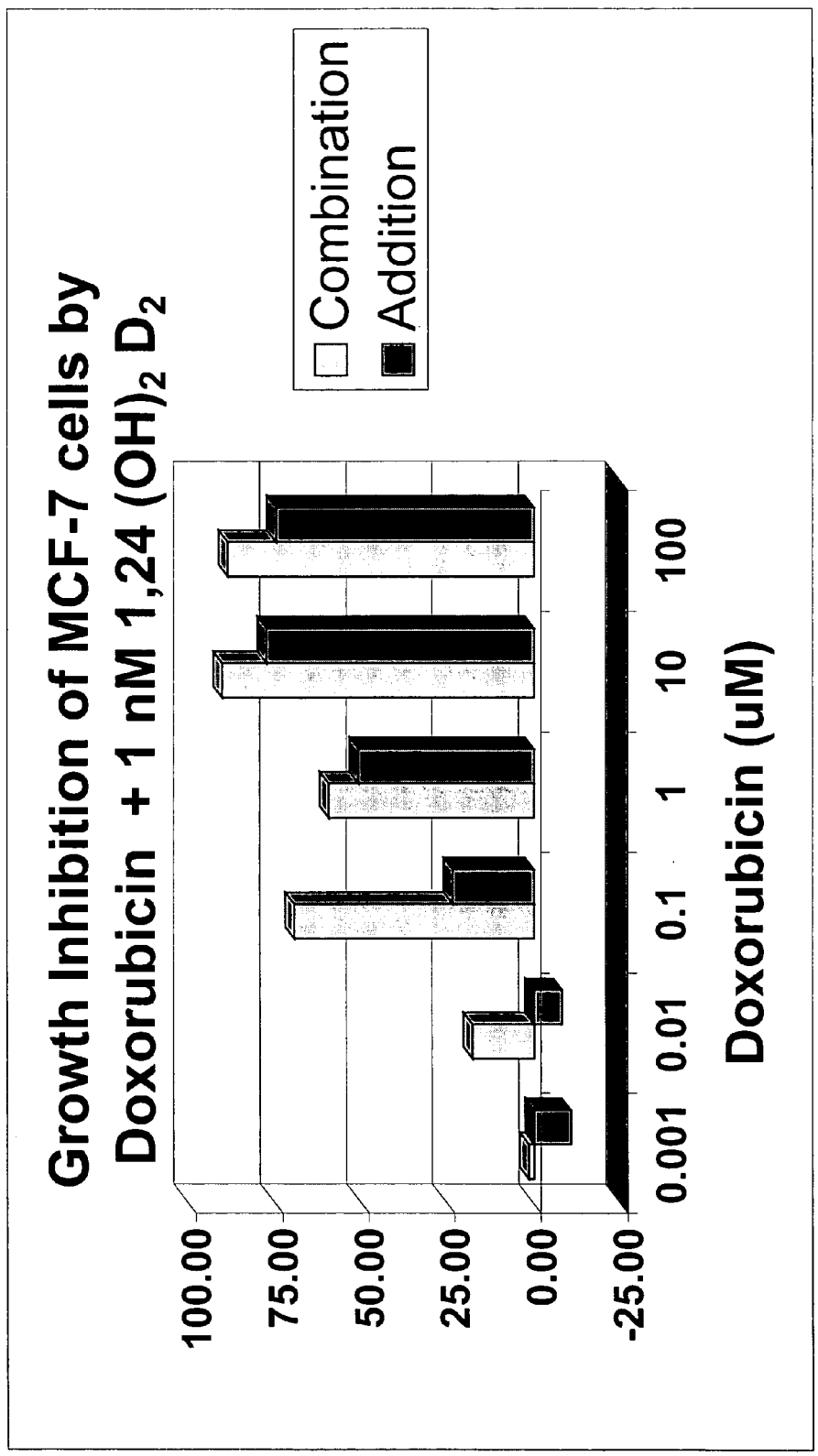
FIG. 9 shows the growth inhibition of MCF-7 cells by doxorubicin and 1 nM 1α,24-dihydroxyvitamin $D_2$.
Figure 10:
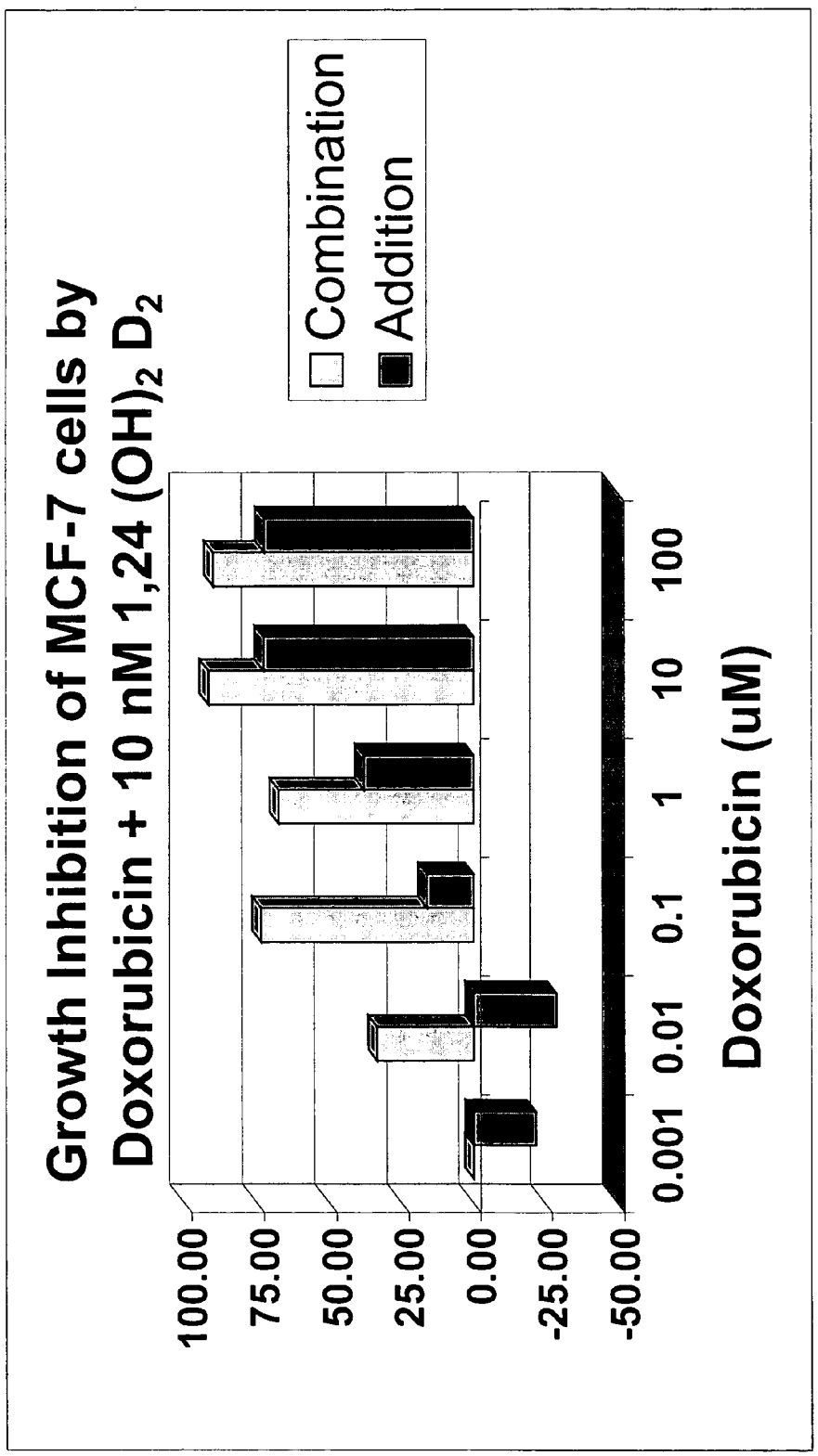
FIG. 10 shows the growth inhibition of MCF-7 cells by doxorubicin and 10 nM 1α,24-dihydroxyvitamin $D_2$.

MCF-7 cells were plated in 96-well plates in triplicate and allowed to grow 48 hours. The medium was removed and replaced with medium containing vehicle (Ethanol), $1,24(OH)_2D_2$ in various concentrations, and doxorubicin in various concentrations. Cells were allowed to grow for an additional 6 days with media changed on day 3. Cell number was then determined by a colorimetric MTS assay and expressed as a % of change from control cells grown in vehicle only. FIG. 5 shows the percent inhibition of MCF-7 cells of doxorubicin alone or in combination with various concentrations of $1,24(OH)_2D_2$. ID30 values (dose required to inhibit proliferation by 30%) were calculated to compare growth inhibitory effects of the compounds alone and in combination. Isobologram analysis was used to characterize the interaction between $1,24(OH)_2D_2$ and doxorubicin as synergistic, additive, or antagonistic. The isobologram is shown in FIG. 6, and shows that doxorubicin in the concentration range of about 0 to 0.15 µM when combined with $1,24(OH)_2D_2$ of various concentrations can provide a synergistic effect. This effect can also be seen in FIGS. 7–10. FIGS. 7–10 show that in certain concentrations, doxorubicin can have a synergistic effect when combined with $1,24(OH)_2D_2$. In FIGS. 7–10 the addition columns show the amount of inhibition predicted if the combination of doxorubicin and $1,24(OH)_2D_2$ simply had an additive effect on each other. The growth inhibition chart of FIG. 7 shows that the combination of doxorubicin in concentrations of 0.01 µM, 0.1 µM, 1 µM, 10 µM and 100 µM with 0.01 nM of $1,24(OH)_2D_2$ produces synergistic growth inhibition. The growth inhibition chart of FIG. 8 shows that the combination of doxorubicin in concentrations of 1 µM, 10 µM and 100 µM with 0.1 nM of $1,24(OH)_2D_2$ produces synergistic growth inhibition. The growth inhibition chart of FIG. 9 shows that the combination of doxorubicin in concentrations of 0.001 µM, 0.01 µM, 0.1 µM, 1 µM, 10 µM and 100 µM with 1 nM of $1,24(OH)_2D_2$ produces synergistic growth inhibition. The growth inhibition chart of FIG. 10 shows that the combination of doxorubicin in concentrations of 0.01 µM, 0.01 µM, 1 µM, 10 µM and 100 µM with 10 nM of $1,24(OH)_2D_2$ produces synergistic growth inhibition.

Example 12

Growth Inhibition of MCF-7 Cells by Tamoxifen and with $1,24(OH)_2D_2$

Figure 11:
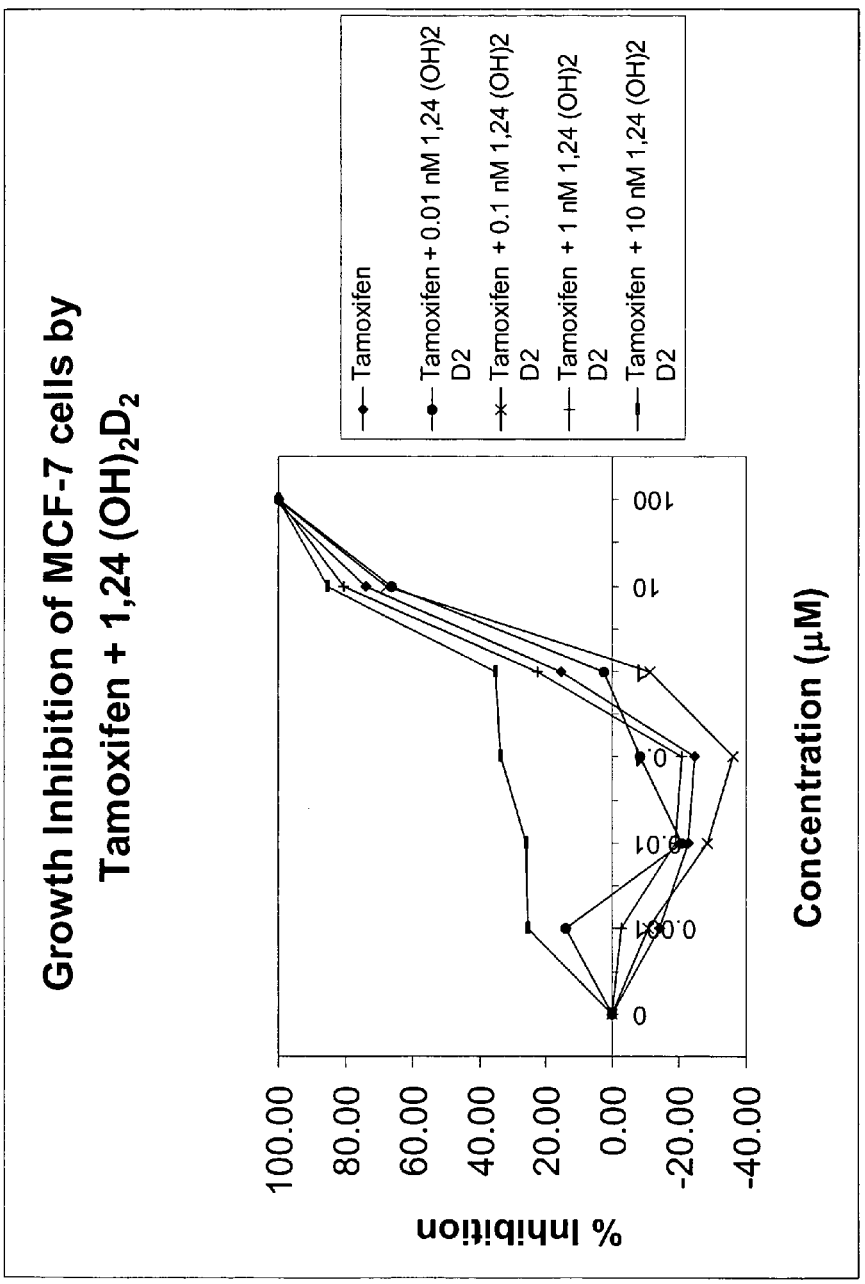
FIG. 11 shows the growth inhibition of MCF-7 cells by tamoxifen and 1α,24-dihydroxyvitamin $D_2$.
Figure 12:
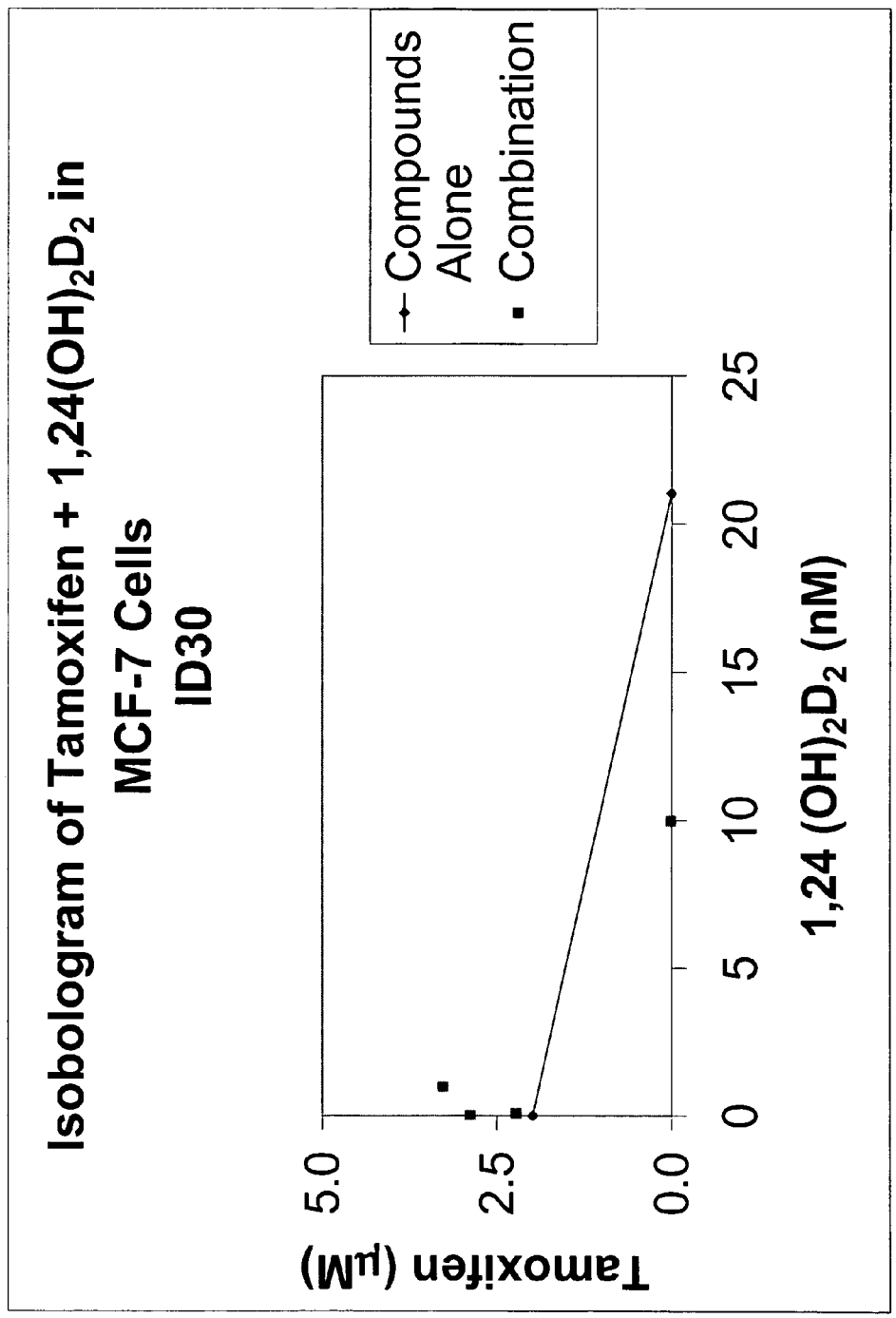
FIG. 12 shows an isobologram of tamoxifen and 1α,24-dihydroxyvitamin $D_2$ in MCF-7 cells.
Figure 13:
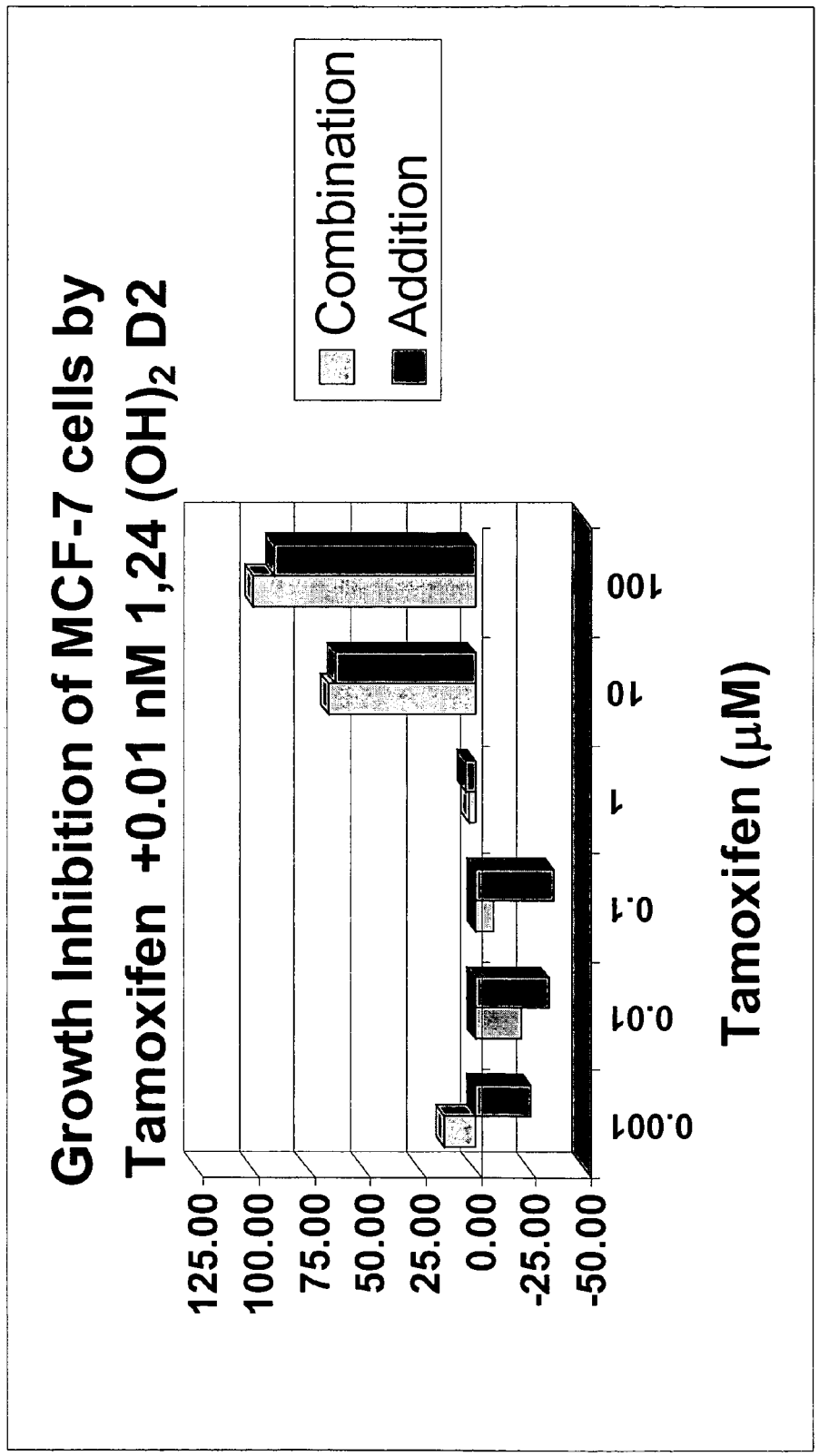
FIG. 13 shows the growth inhibition of MCF-7 cells by tamoxifen and 0.01 nM 1α,24-dihydroxyvitamin $D_2$.
Figure 14:
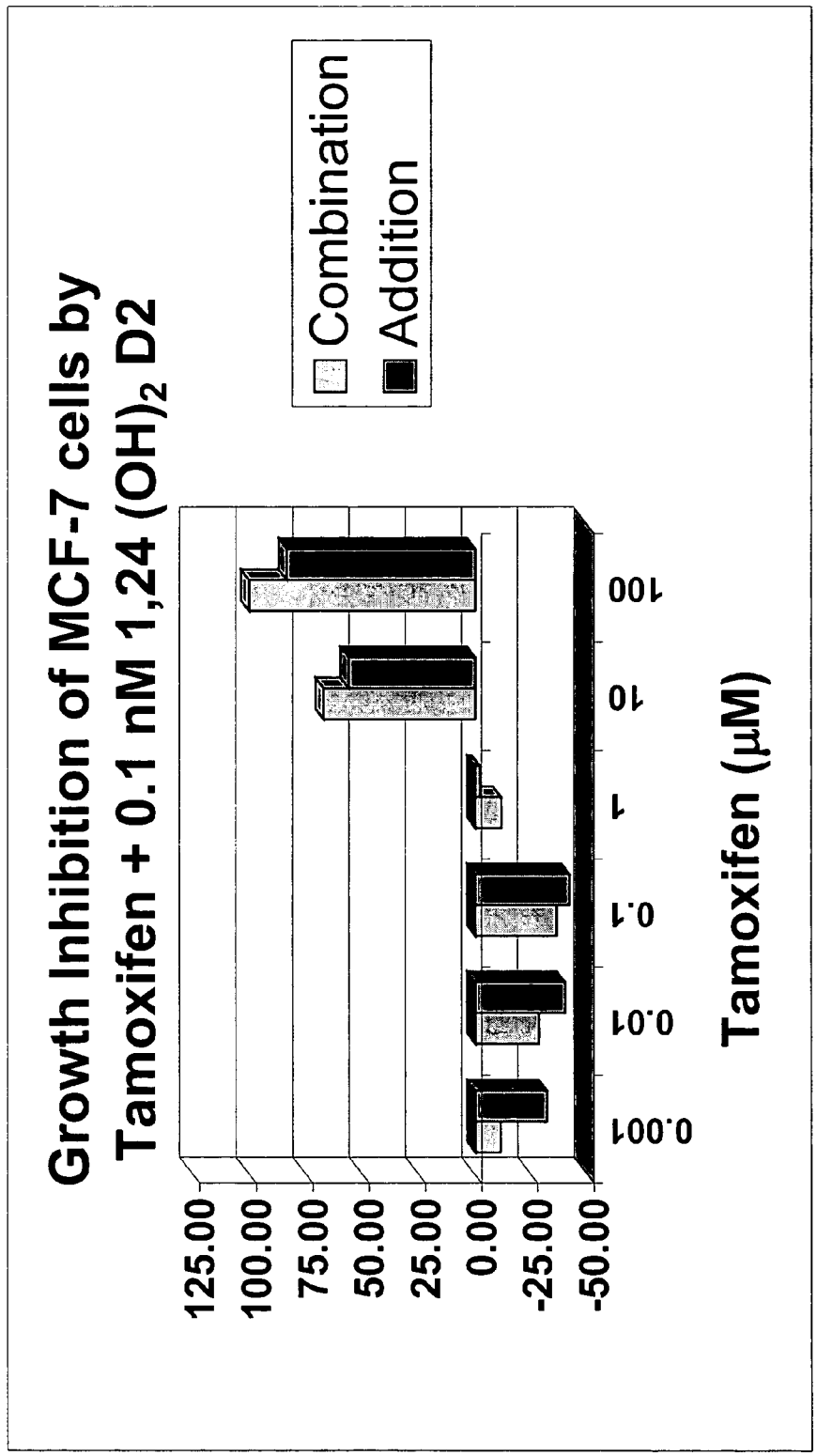
FIG. 14 shows the growth inhibition of MCF-7 cells by tamoxifen and 0.1 nM 1α,24-dihydroxyvitamin $D_2$.

MCF-7 cells were plated in 96-well plates in triplicate and allowed to grow 48 hours. The medium was removed and replaced with medium containing vehicle (Ethanol), $1,24(OH)_2D_2$ in various concentrations, and tamoxifen in various concentrations. Cells were allowed to grow for an additional 6 days with media changed on day 3. Cell number was then determined by a colorimetric MTS assay and expressed as a % of change from control cells grown in vehicle only. FIG. 11 shows the percent inhibition of MCF-7 cells of tamoxifen alone or in combination with various concentrations of $1,24(OH)_2D_2$. ID30 values (dose required to inhibit proliferation by 30%) were calculated to compare growth inhibitory effects of the compounds alone and in combination. Isobologram analysis was used to characterize the interaction between $1,24(OH)_2D_2$ and tamoxifen as synergistic, additive, or antagonistic. The isobologram is shown in FIG. 12. In FIGS. 13–14 the addition columns show the amount of inhibition predicted if the combination of tamoxifen and $1,24(OH)_2D_2$ simply had an additive effect on each other. The growth inhibition chart of FIG. 13 shows that the combination of tamoxifen in concentrations of 10 µM and 100 µM with 0.01 nM of $1,24(OH)_2D_2$ produces additive to mild synergistic growth inhibition. The growth inhibition chart of FIG. 14 shows that the combination of tamoxifen in concentrations of 10 µM and 100 µM with 0.1 nM of $1,24(OH)_2D_2$ produces additive to mild synergistic growth inhibition.

Example 13

Growth Inhibition of MCF-7 Cells by Chlorambucil and with $1,24(OH)_2D_2$

Figure 15:
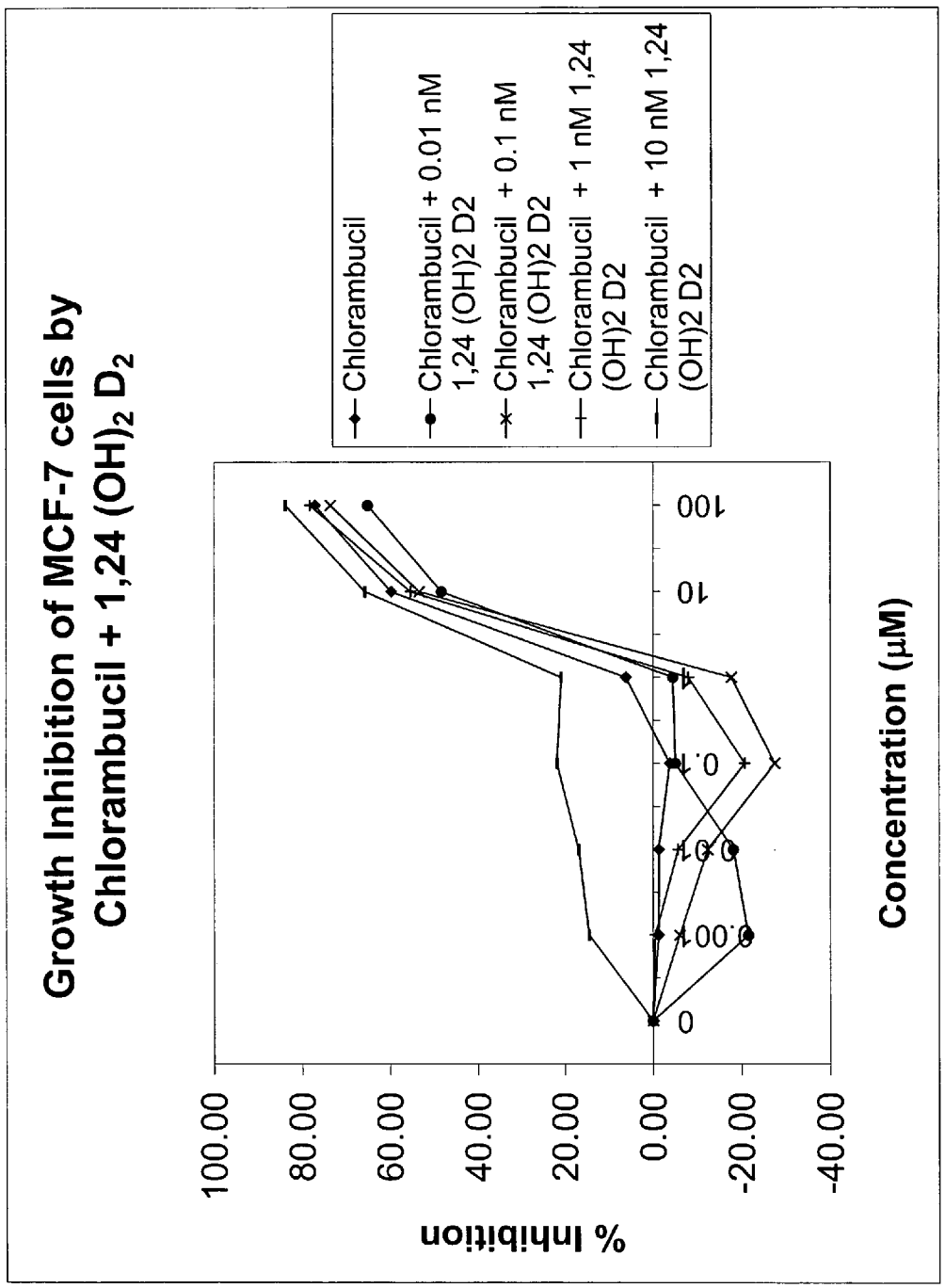
FIG. 15 shows the growth inhibition of MCF-7 cells by chlorambucil and 1α,24-dihydroxyvitamin $D_2$.
Figure 16:
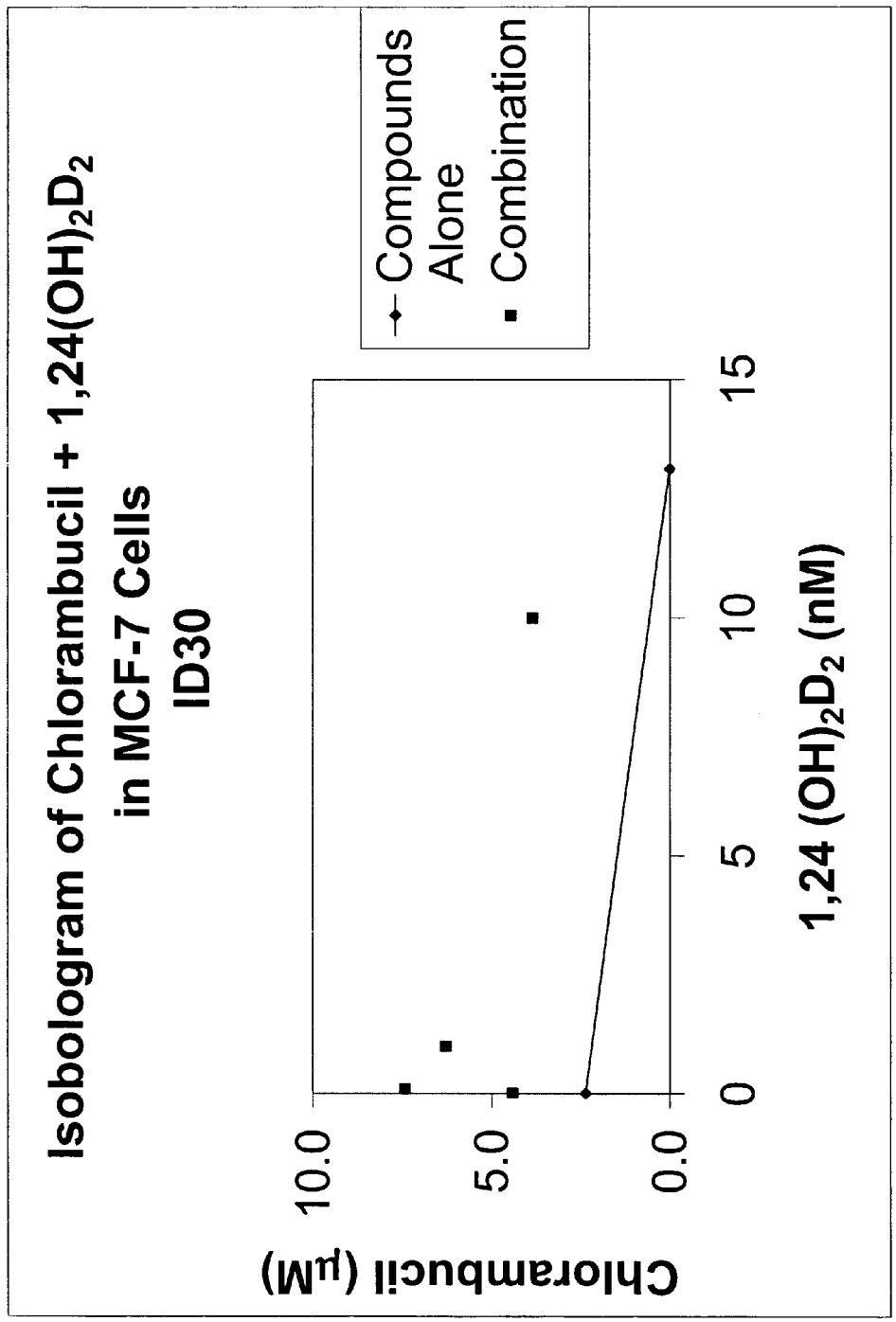
FIG. 16 shows an isobologram of chlorambucil and 1α,24-dihydroxyvitamin $D_2$ in MCF-7 cells.
Figure 17:
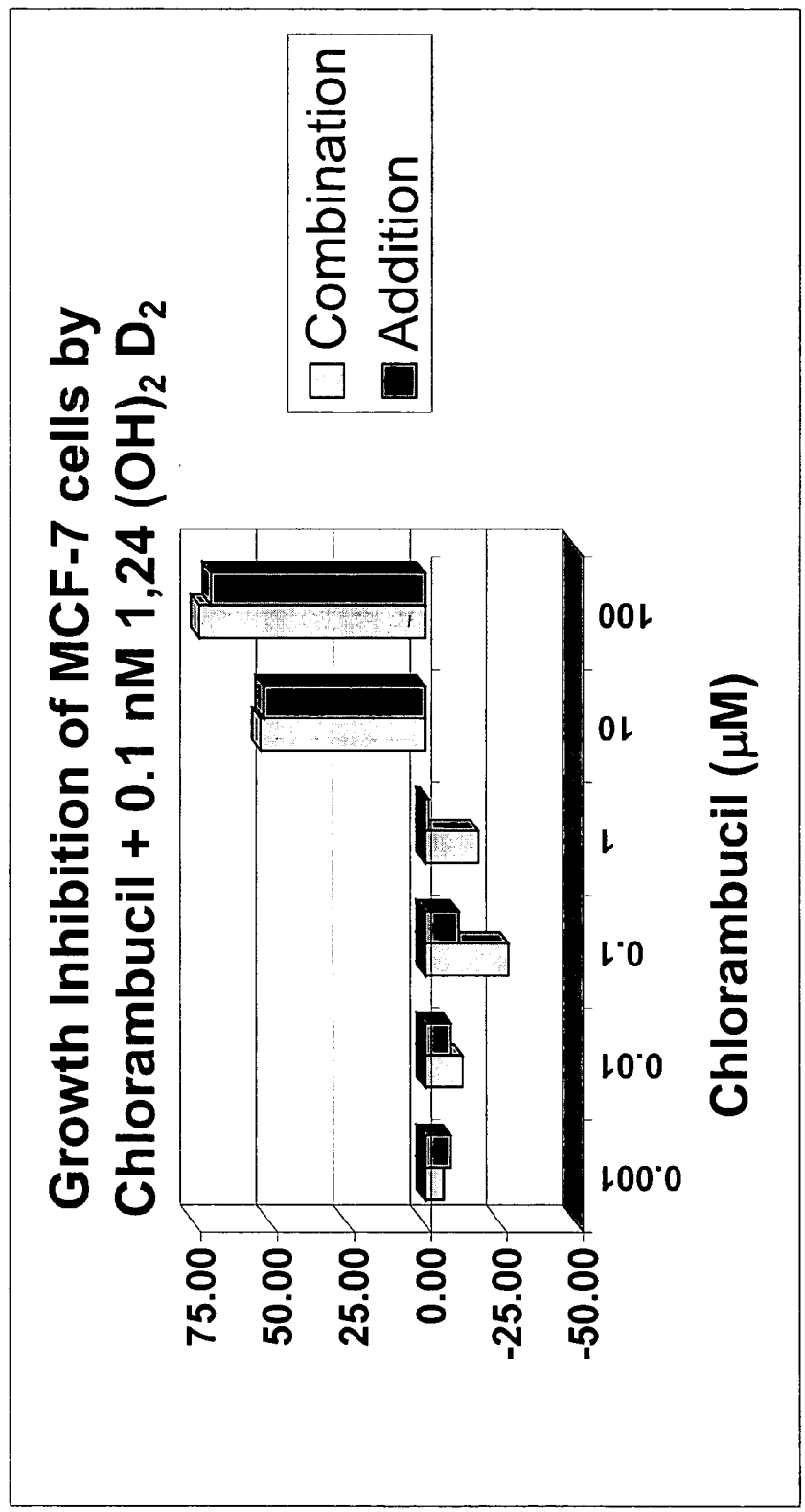
FIG. 17 shows the growth inhibition of MCF-7 cells by chlorambucil and 0.1 nM 1α,24-dihydroxyvitamin $D_2$.

MCF-7 cells were plated in 96-well plates in triplicate and allowed to grow 48 hours. The medium was removed and replaced with medium containing vehicle (Ethanol), 1,24 (OH)$_2$D$_2$ in various concentrations, and chlorambucil in various concentrations. Cells were allowed to grow for an additional 6 days with media changed on day 3. Cell number was then determined by a colorimetric MTS assay and expressed as a % of change from control cells grown in vehicle only. FIG. 15 shows the percent inhibition of MCF-7 cells of chlorambucil alone or in combination with various concentrations of 1,24(OH)$_2$D$_2$. ID30 values (dose required to inhibit proliferation by 30%) were calculated to compare growth inhibitory effects of the compounds alone and in combination. Isobologram analysis was used to characterize the interaction between 1,24(OH)$_2$D$_2$ and chlorambucil as synergistic, additive, or antagonistic. The isobologram is shown in FIG. 16. FIG. 17 shows that in certain concentrations, chlorambucil can have an additive effect when combined with 1,24(OH)$_2$D$_2$. In FIG. 17 the addition columns show the amount of inhibition predicted if the combination of chlorambucil and 1,24(OH)$_2$D$_2$ simply had an additive effect on each other. The growth inhibition chart of FIG. 17 shows that the combination of chlorambucil in various concentrations produces antagonistic to mild additive growth inhibition.

Example 14

Growth Inhibition of MCF-7 Cells by Busulfan and 1,24(OH)$_2$D$_2$

Figure 18:
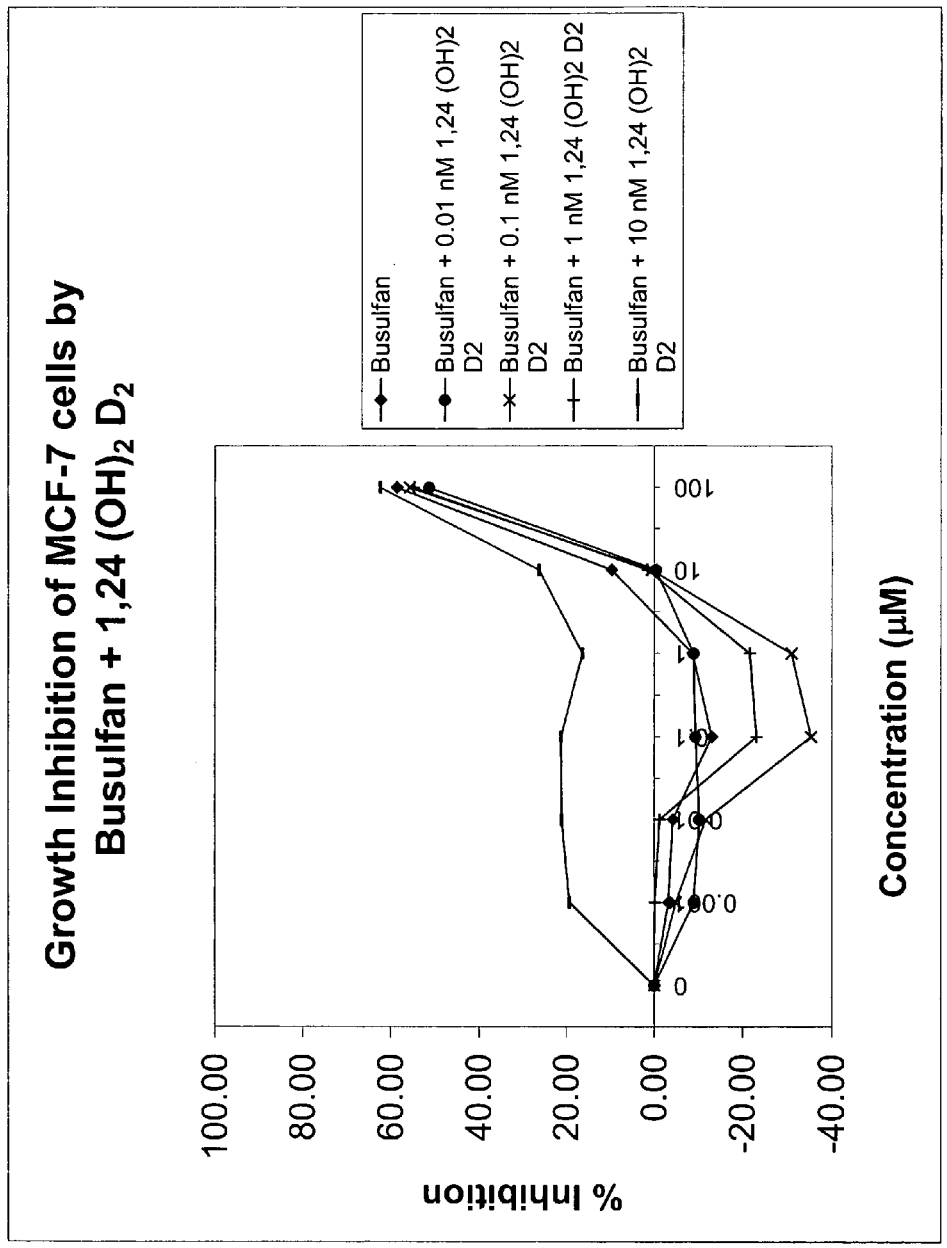
FIG. 18 shows the growth inhibition of MCF-7 cells by busulfan and 1α,24-dihydroxyvitamin $D_2$.
Figure 19:
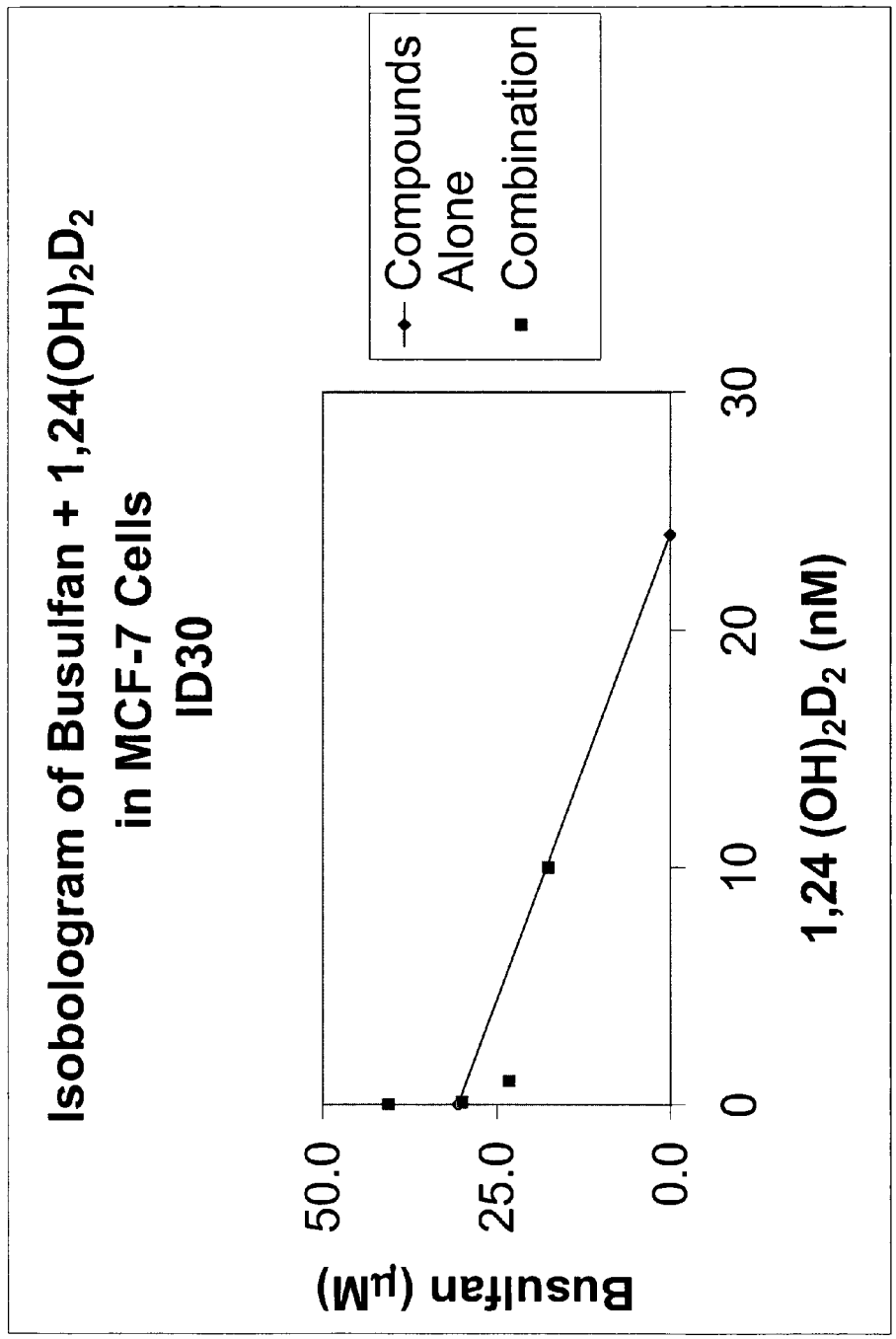
FIG. 19 shows an isobologram of busulfan and 1α,24-dihydroxyvitamin $D_2$ in MCF-7 cells.
Figure 20:
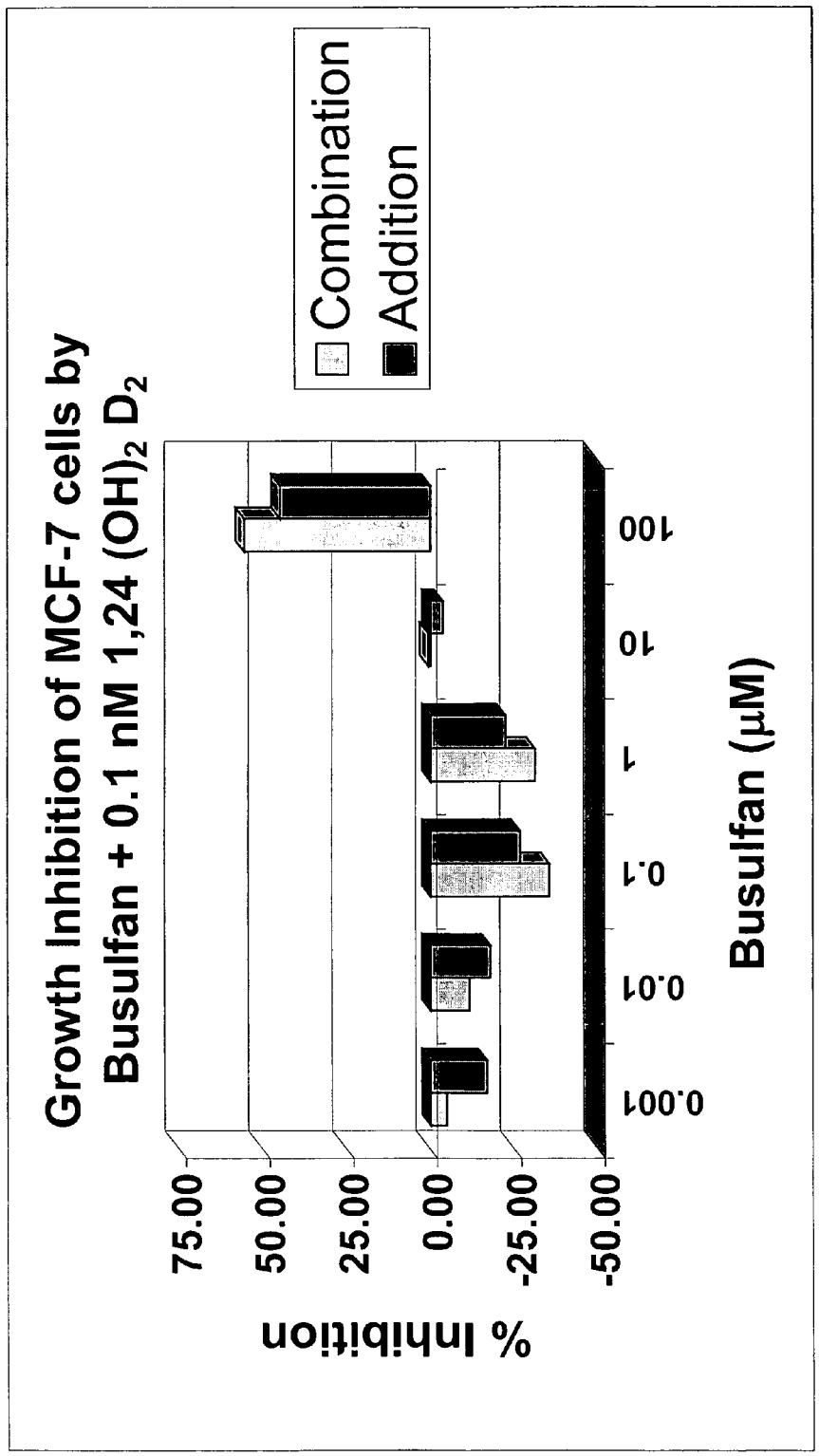
FIG. 20 shows the growth inhibition of MCF-7 cells by busulfan and 0.1 nM 1α,24-dihydroxyvitamin $D_2$.

MCF-7 cells were plated in 96-well plates in triplicate and allowed to grow 48 hours. The medium was removed and replaced with medium containing vehicle (Ethanol), 1,24 (OH)$_2$D$_2$ in various concentrations, and busulfan in various concentrations. Cells were allowed to grow for an additional 6 days with media changed on day 3. Cell number was then determined by a colorimetric MTS assay and expressed as a % of change from control cells grown in vehicle only. FIG. 18 shows the percent inhibition of MCF-7 cells of busulfan alone or in combination with various concentrations of 1,24(OH)$_2$D$_2$. ID30 values (dose required to inhibit proliferation by 30%) were calculated to compare growth inhibitory effects of the compounds alone and in combination. Isobologram analysis was used to characterize the interaction between 1,24(OH)$_2$D$_2$ and busulfan as synergistic, additive, or antagonistic. The isobologram is shown in FIG. 19. In FIG. 20 the addition columns show the amount of inhibition predicted if the combination of busulfan and 1,24(OH)$_2$D$_2$ simply had an additive effect on each other. The growth inhibition chart of FIG. 20 shows that the combination of busulfan in concentrations of 100 μM with 0.1 nM of 1,24(OH)$_2$D$_2$ produces mild synergistic growth inhibition.

Example 15

Combination Index (CI) Values for Chemotherapeutic Drugs and 1,24(OH)$_2$D$_2$ Combinations in MCF-7 Cells As shown in FIG. 21, 1,24(OH)$_2$D$_2$ was dosed in combination with individual anticancer agents at several different molar ratios. The degree of interaction between two drugs was calculated using the combination index, according to the isobologram equation:

$$CI = d_1/D_1 + d_2/D_2.$$

In this equation, $d_1$ and $d_2$ represent the doses of drug 1 and drug 2 that, when given in combination, produce a specific response, and $D_1$ and $D_2$ represent the doses of drug 1 and drug 2 when given individually, produce the same effect. Drug interactions determined by the Combination Index were classified according to the following criteria:

| Combination Index (CI) | Drug Interaction Description |
| --- | --- |
| <0.1 | Very Strong Synergism |
| 0.1–0.3 | Strong Synergism |
| 0.3–0.7 | Synergism |
| 0.7–0.85 | Moderate Synergism |
| 0.85–0.90 | Slight Synergism |
| 0.90–1.10 | Additive |
| 1.10–1.20 | Slight Antagonism |
| 1.20–1.45 | Moderate Antagonism |
| 1.45–3.3 | Antagonism |
| 3.3–10 | Strong Antagonism |
| >10 | Very Strong Antagonism |

Multiple trials were run to determine a p value for the combination index for the drug combinations. Degree of interaction is defined as significant at p<0.075.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation lawfully accorded the appended claims.

All patents, publications and references cited herein are hereby fully incorporated by reference. In case of conflict between the present disclosure and incorporated patents, publications and references, the present disclosure should control.

What is claimed is:

1. A method of synergistically inhibiting the growth of human breast cancer cells, comprising contacting the cells with a first composition which comprises 1α,24-dihydroxyvitamin D$_2$ and a second composition which comprises an agent selected from the group consisting of doxorubicin, cisplatin and paclitaxel or combinations thereof.

2. The method of claim 1 wherein the agent is doxorubicin.

3. The method of claim 1 wherein the agent is cisplatin.

4. The method of claim 1 wherein the agent is paclitaxel.

5. The method of claim 1, wherein the first and second compositions are administered to a human cancer patient.

6. The method of claim 5 wherein the first and second compositions are co-administered.

7. The method of claim 5 wherein the first and second compositions are administered in a daily regimen.

8. The method of claim 5 wherein the first and second compositions are administered in an episodic regimen.

9. The method of claim 5 wherein the first composition is administered intravenously.

10. The method of claim 5 wherein the first composition is administered orally.

11. The method of claim 5 wherein the first composition is administered in an amount of 0.01 μg to 400 μg of 1α,24-dihydroxyvitamin D$_2$.

* * * * *